US011739151B2

(12) United States Patent
Liu et al.

(10) Patent No.: US 11,739,151 B2
(45) Date of Patent: Aug. 29, 2023

(54) ANTI-PD-L1/ANTI-CD47 BISPECIFIC ANTIBODY

(71) Applicant: Beijing Hanmi Pharmaceutical Co., Ltd., Beijing (CN)

(72) Inventors: Jiawang Liu, Beijing (CN); Yaping Yang, Beijing (CN); Nanmeng Song, Beijing (CN); Maengsup Kim, Beijing (CN)

(73) Assignee: Beijing Hanmi Pharmaceutical Co., Ltd., Beijing (CN)

( * ) Notice: Subject to any disclaimer, the term of this patent is extended or adjusted under 35 U.S.C. 154(b) by 381 days.

(21) Appl. No.: 16/769,108

(22) PCT Filed: Dec. 1, 2018

(86) PCT No.: PCT/CN2018/118800
§ 371 (c)(1),
(2) Date: Jun. 2, 2020

(87) PCT Pub. No.: WO2019/109876
PCT Pub. Date: Jun. 13, 2019

(65) Prior Publication Data
US 2021/0230277 A1 Jul. 29, 2021

(30) Foreign Application Priority Data
Dec. 4, 2017 (CN) .......................... 201711261880.8

(51) Int. Cl.
*C07K 16/28* (2006.01)
*C07K 16/46* (2006.01)
*A61K 39/00* (2006.01)

(52) U.S. Cl.
CPC ........ *C07K 16/2827* (2013.01); *C07K 16/468* (2013.01); *A61K 2039/505* (2013.01); *C07K 2317/31* (2013.01); *C07K 2317/55* (2013.01); *C07K 2317/569* (2013.01); *C07K 2317/622* (2013.01)

(58) Field of Classification Search
CPC .................. C07K 16/468; A61K 2039/505
USPC .................................... 424/133.1
See application file for complete search history.

(56) References Cited

U.S. PATENT DOCUMENTS

| 8,217,149 | B2 | 7/2012 | Irving et al. | |
|---|---|---|---|---|
| 10,239,945 | B2 * | 3/2019 | Manning | A61P 37/02 |
| 10,844,124 | B2 * | 11/2020 | Manning | A61P 9/14 |
| 11,319,378 | B2 * | 5/2022 | Liu | C07K 16/2818 |
| 11,498,977 | B2 * | 11/2022 | Liu | C07K 16/2887 |
| 11,529,425 | B2 * | 12/2022 | Xu | C07K 16/2827 |
| 2006/0074225 | A1 | 4/2006 | Chamberlain et al. | |
| 2013/0195849 | A1 | 8/2013 | Spreter Von Kreudenstein et al. | |
| 2013/0336981 | A1 | 12/2013 | de Kruif et al. | |
| 2018/0171014 | A1 * | 6/2018 | Manning | A61P 43/00 |
| 2019/0300611 | A1 * | 10/2019 | Manning | A61P 37/06 |
| 2021/0070865 | A1 * | 3/2021 | Manning | A61P 1/04 |
| 2021/0162061 | A1 * | 6/2021 | Xu | C07K 16/2827 |
| 2023/0090014 | A1 * | 3/2023 | Xiao | A61K 38/16 |

FOREIGN PATENT DOCUMENTS

| CN | 102245640 A | 11/2011 |
|---|---|---|
| CN | 103429620 A | 12/2013 |
| CN | 106883297 A | 6/2017 |
| JP | 2012/511329 A | 5/2012 |
| WO | WO-2014/087248 A2 | 6/2014 |
| WO | WO-2016/023001 A1 | 2/2016 |
| WO | WO-2016/024021 A1 | 2/2016 |
| WO | WO-2016/109415 A1 | 7/2016 |
| WO | WO-2017/027422 A1 | 2/2017 |
| WO | WO-2017/101828 A1 | 6/2017 |
| WO | WO-2017/167919 A1 | 10/2017 |
| WO | WO-2019/068302 A1 | 4/2019 |

OTHER PUBLICATIONS

Calles et al. (Clinical and Translational Oncology (2019) 21:961-976).*
Chauchetetal (Cancer Research, (Jun. 2022) vol. 82, No. 12, Supp. Supplement. Abstract No. 3428. Meeting Info: American Association for Cancer Research Annual Meeting, ACCR 2020. New Orleans, LA, United States. Apr. 8, 2022-Apr. 13, 2022).*
Chauchetetal (Cancer Research, (Jun. 2022) vol. 82, No. 12, Supp. Supplement. Abstract No. 3429. Meeting Info: American Association for Cancer Research Annual Meeting, ACCR 2020. New Orleans, LA, United States. Apr. 8, 2022-Apr. 13, 2022).*
Chauchet et al. (Journal for ImmunoTherapy of Cancer, (Nov. 2021) vol. 9, No. SUPPL 2, pp. A287. Abstract No. 265. Meeting Info: 36th Annual Meeting of the Society for Immunotherapy of Cancer's, SITC 2021. Virtual. Nov. 11, 2021-Nov. 14, 2021).*
Liu etal (MABS vol. 10, No. 2, 315-324 (2018)).*
Bian et al. (Biomedicines 2022, 10, 1843; Jul. 30, 2022).*
International Search Report for International Application No. PCT/CN2018/118800 dated Mar. 4, 2019.
Liu Boning., "Construction and anti-tumor effects of a novel bispecific fusion protein targeting pd-L1 and cd47," South China University of Technology: 122 pages (2016).
Sockolosky et al., "Durable antitumor responses to CD47 blockade require adaptive immune stimulation," PNAS, 113(19): E2646-E2654 (2016).
Von Kreudenstein et al., "Improving biophysical properties of a bispecific antibody scaffold to aid developability," mAbs, 5(5): 646-654 (2013).

* cited by examiner

*Primary Examiner* — Lynn A Bristol
(74) *Attorney, Agent, or Firm* — Foley Hoag LLP; Dana M. Gordon; Mohanad Mossalam

(57) ABSTRACT

Provided are an anti-PD-L1/anti-CD47 bispecific antibody that has natural IgG characteristics and is in a highly stable heterodimer form without the heavy chain and light chain being mismatched, and a preparation method therefor. Either the first Fc chain or second Fc chain of the bispecific antibody comprises amino acid substitutions at positions 366 and 399, and the other comprises amino acid substitutions at positions 351, 407 and 409.

18 Claims, 9 Drawing Sheets

Specification includes a Sequence Listing.

ANTI-PD-L1/ANTI-CD47 BISPECIFIC ANTIBODY

CROSS-REFERENCE TO RELATED APPLICATIONS

This application is a 371 U.S. national stage application of PCT/CN2018/118800, filed on Dec. 1, 2018, which claims the benefit of priority to China patent application serial number 201711261880.8, filed on Dec. 4, 2017.

SEQUENCE LISTING

The instant application contains a Sequence Listing which has been submitted electronically in ASCII format and is hereby incorporated by reference in its entirety. Said ASCII copy is named CNX-00501_SL.txt and is 18,363 bytes in size.

TECHNICAL FIELD

The invention relates to an anti-PD-L1/anti-CD47 bispecific antibody with a structure like natural antibody and in the form of a heterodimer, and preparation thereof. Specifically, the present invention provides an anti-PD-L1/anti-CD47 bispecific antibody that has natural IgG characteristics and is in the form of a highly stable heterodimer without the heavy chain and light chain mismatch, and a preparation method therefor.

BACKGROUND

Programmed death ligand 1 (PD-L1) is a ligand of immune checkpoint programmed death-1 (PD-1), and belongs to the B7 family and is induced to be expressed at the surfaces of various immune cells, including T cells, B cells, monocytes, macrophages, DC cells and endothelial cells, epidermal cells, etc. After PD-L1 binds to PD-1, it is mainly involved in the negative regulation of T cell activation, which can adjust the strength and duration of the immune response. In addition to being a PD-1 ligand, PD-L1 can also serve as a ligand for CD80, transmit negative regulatory signals to T cells and induce immune tolerance of T cells (Autoimmun Rev, 2013, 12(11): 1091-1100. Front Immunol, 2013, 4: 481. Nat Rev Cancer, 2012, 12(4): 252-264. Trends Mol Med. 2015 January; 21(1):24-33. Clin Cancer Res. 2012 Dec. 15; 18(24):6580-7). Under normal circumstances, PD-L1 and PD-1 can mediate and maintain autoimmune tolerance of the tissues of the body, prevent the immune system from being excessively activated to damage own tissues of the body during the inflammatory reaction, and have positive effects on avoiding the occurrence of autoimmune diseases. Under pathological conditions, it is involved in the occurrence and development of tumor immunity and various autoimmune diseases. A number of studies have reported that PD-L1 is highly expressed in various tumor tissues, and PD-1 is highly expressed in tumor-infiltrating lymphocytes, and the overexpression of PD-L1 and PD-1 is closely related to the poor clinical prognosis of tumors (Anticancer Agents Med Chem. 2015; 15(3):307-13. Hematol Oncol Stem Cell Ther. 2014 March; 7(1):1-17. Trends Mol Med. 2015 January; 21(1):24-33. Immunity. 2013 Jul. 25; 39(1):61-73. J Clin Oncol. 2015 Jun. 10; 33(17):1974-82). The use of PD-L1 monoclonal antibodies to block the interaction of PD-L1/PD-1 and CD80/PD-L1 has shown good anti-tumor effects in pre-clinical experimental studies and clinical trials. At present, PD-L1 monoclonal antibodies have been approved for the treatment of various tumors such as non-small cell lung cancer and urothelial cancer. However, only a small percentage of tumor patients can benefit from this type of monoclonal antibody therapy, and most patients do not respond to this type of monoclonal antibodies (Expert Opin Ther Targets. 2014 December; 18(12):1407-20. Oncology (Williston Park). 2014 November; 28 Suppl 3:15-28).

CD47, also called integrin-related protein, is a 50 kD transmembrane protein and belongs to the immunoglobulin superfamily. It is widely expressed on a variety of cells, but its expression is significantly enhanced on a variety of tumor cells (Proc Natl Acad Sci USA, 2012, 109(17): 6662-6667). The ligand of CD47 is signal-regulatory protein α (SIRPα), which is mainly expressed in macrophages. After binding to CD47, it transmits the signal of "don't eat me" and inhibits the phagocytosis of macrophages (Curr Opin Immunol, 2009, 21(1):47-52). The use of anti-CD47 antibodies can block the CD47-SIRPα signaling pathway, and thereby exerts an anti-tumor effect. At present, a variety of anti-CD47 monoclonal antibodies have been entered the clinical research stage for the treatment of various hematological and solid tumors. However, since CD47 is also expressed on the surface of erythrocytes, these anti-CD47 treatments may lead to serious adverse reactions such as anemia and thrombocytopenia, and low bioavailability.

There is still a need in this field to study a novel therapeutic drug that blocks both PD-L1 and CD47 signaling pathways.

SUMMARY OF THE INVENTION

The present invention provides a novel bifunctional antibody that can block PD-L1 and CD47 at the same time and has a highly stable heterodimer form with natural IgG structural characteristics and no heavy chain and light chain mismatch, and a preparation method therefor. The bifunctional antibody tends to selectively bind to tumor cells that simultaneously express PD-L1 and CD47, and thereby exerts efficient and specific killing effects, while has low toxic and side effects.

The first aspect of the present invention relates to a bispecific antibody in the form of a heterodimer, which comprises a first Fc chain and a second Fc chain, and a first antigen-binding functional region that can specifically bind to PD-L1 and a second antigen-binding functional region that can specifically bind to CD47;

wherein each of the first Fc chain and the second Fc chain is an immunoglobulin G Fc fragment comprising an amino acid substitution, and the first Fc chain and the second Fc chain together constitute a heterodimer that can bind to an Fc receptor;

wherein the first Fc chain and the second Fc chain are linked to the first antigen-binding functional region and the second antigen-binding functional region by a covalent bond or a linker, respectively; and wherein either one of the first Fc chain and the second Fc chain comprises amino acid substitutions at positions 366 and 399, and the other comprises amino acid substitutions at positions 351, 407, and 409, wherein the amino acid positions are numbered according to Kabat EU Index numbering system.

The first Fc chain and the second Fc chain herein are defined only for the purpose of distinguishing the two existing Fc chains, and it does not mean that the importance or order thereof is different. At the same time, the linkage of the first Fc chain and the second Fc chain to the first antigen-binding functional region and the second antigen-binding functional region is also arbitrary. That is, the first Fc chain can be linked to the first antigen-binding functional region or to the second antigen binding domain, and so is the second Fc chain.

In some embodiments, the first Fc chain and the second Fc chain amino acid substitutions are as follows:

a) L351G, L351Y, L351V, L351P, L351D, L351E, L351K or L351W;

b) T366L, T366P, T366W or T366V;

c) D399C, D399N, D399I, D399G, D399R, D399T or D399A;

d) Y407L, Y407A, Y407P, Y407F, Y407T or Y407H; and e) K409C, K409P, K409S, K409F, K409V, K409Q or K409R.

In some embodiments, the amino acid substitutions comprise:

a) T366L and D399R substitutions in either one of the first Fc chain and the second Fc chain, and L351E, Y407L and K409V substitutions in the other;

b) T366L and D399C substitutions in either one of the first Fc chain and the second Fc chain, and L351G, Y407L and K409C substitutions in the other;

c) T366L and D399C substitutions in either one of the first Fc chain and the second Fc chain, and L351Y, Y407A and K409P substitutions in the other;

d) T366P and D399N substitutions in either one of the first Fc chain and the second Fc chain, and L351V, Y407P and K409S substitutions in the other;

e) T366W and D399G substitutions in either one of the first Fc chain and the second Fc chain, and L351D, Y407P and K409S substitutions in the other;

f) T366P and D399I substitutions in either one of the first Fc chain and the second Fc chain, and L351P, Y407F and K409F substitutions in the other;

g) T366V and D399T substitutions in either one of the first Fc chain and the second Fc chain, and L351K, Y407T and K409Q substitutions in the other;

h) T366L and D399A substitutions in either one of the first Fc chain and the second Fc chain, and L351W, Y407H, and K409R substitutions in the other.

In some embodiments, the amino acid substitutions comprise:

a) T366L and K409V substitutions in either one of the first Fc chain and the second Fc chain, and L351E, Y407L and D399R substitutions in the other;

b) T366L and K409C substitutions in either one of the first Fc chain and the second Fc chain, and L351G, Y407L and D399C substitutions in the other;

c) T366L and K409P substitutions in either one of the first Fc chain and the second Fc chain, and L351Y, Y407A and D399C substitutions in the other;

d) T366P and K409S substitutions in either one of the first Fc chain and the second Fc chain, and L351V, Y407P and D399N substitutions in the other;

e) T366W and K409S substitutions in either one of the first Fc chain and the second Fc chain, and L351D, Y407P and D399G substitutions in the other;

f) T366P and K409F substitutions in either one of the first Fc chain and the second Fc chain, and L351P, Y407F and D399I substitutions in the other;

g) T366V and K409Q substitutions in either one of the first Fc chain and the second Fc chain, and L351K, Y407T and D399T substitutions in the other;

h) T366L and K409R substitutions in either one of the first Fc chain and the second Fc chain, and L351W, Y407H and D399A substitutions in the other.

In some embodiments, the amino acids in either one of the first Fc chain and the second Fc chain are substituted by T366L and D399R, and the amino acids of the other are substituted by L351E, Y407L, and K409V.

In some embodiments, the first antigen-binding functional region and the second antigen-binding functional region are selected from a Fab fragment, a scFv fragment, a variable domain fragment Fv, and a heavy chain variable region fragment VHH of a heavy chain antibody.

In some embodiments, the first antigen-binding functional region and the second antigen-binding functional region are both Fab fragments.

In some embodiments, one of the first antigen-binding functional region and the second antigen-binding functional region is a Fab fragment, and the other is a scFv.

In some embodiments, the Fab fragment comprises different first heavy chain variable region and second heavy chain variable region, and different first light chain variable region and second light chain variable region.

In some embodiments, the first Fc chain and the first antigen-binding functional region covalently linked thereto, and the second Fc chain and the second antigen-binding functional region covalently linked thereto, when in a solution in which a reducing agent is present and which comprises no other polypeptide in addition to the first Fc chain and the first antigen-binding functional region covalently linked thereto, and the second Fc chain and the second antigen-antigen binding functional region covalently linked thereto, form less than 50% of homodimers based on the weight of all polypeptide chains.

In some embodiments, the first antigen binding functional region comprises the amino acid sequences of SEQ ID NOs: 2 and 6.

In some embodiments, the second antigen binding functional region comprises the amino acid sequences of SEQ ID NOs: 10 and 12.

In some embodiments, the first antigen binding functional region further comprises the amino acid sequences of SEQ ID NOs: 4 and 8.

In some embodiments, the second antigen binding functional region further comprises the amino acid sequences of SEQ ID NOs: 4 and 14.

In some embodiments, the amino acid sequence of the bispecific antibody is the corresponding combination of SEQ ID NOs: 2, 4, 6, 8, 10, 12, and 14. For example, SEQ ID NOs: 2, 4, 6 and 8 are combined with each other, and SEQ ID NOs: 10, 4, 12 and 14 are combined with each other, and then the combined two are further combined to form the bispecific antibody of the present invention.

The second aspect of the present invention relates to an isolated polynucleotide encoding a bispecific antibody in the form of a heterodimer according to the first aspect.

In some embodiments, the nucleotide sequence encoding the amino acids of the first antigen binding functional region is selected from SEQ ID NOs: 1 and 5.

In some embodiments, the nucleotide sequence encoding the amino acids of the second antigen binding functional region is selected from SEQ ID NOs: 9 and 11.

In some embodiments, the nucleotide sequence encoding the amino acid of the first antigen binding functional region is further selected from SEQ ID NOs: 3 and 7.

In some embodiments, the nucleotide sequence encoding the amino acid of the second antigen binding functional region is further selected from SEQ ID NOs: 3 and 13.

In some embodiments, the sequence of the polynucleotide is the corresponding combination of SEQ ID NOs: 1, 3, 5, 7, 9, 11, and 13. For example, SEQ ID NOs: 1, 3, 5 and 7 are combined with each other, and SEQ ID NOs: 9, 3, 11 and 13 are combined with each other.

The third aspect of the present invention relates to a recombinant expression vector comprising the isolated polynucleotide according to the second aspect.

In some embodiments, the expression vector is a plasmid vector X0GC modified from pCDNA.

The fourth aspect of the present invention relates to a host cell comprising the isolated polynucleotide according to the second aspect, or the recombinant expression vector according to the third aspect.

In some embodiments, the host cell is selected from human embryonic kidney cell HEK293 or HEK293T, HEK293F, HEK293E modified from HEK293 cell; hamster ovary cell CHO or CHO-S, CHO-dhfr⁻, CHO/DG44, ExpiCHO modified from CHO cell; *Escherichia coli* or *Escherichia coli* BL21, BL21(DE3), Rosetta™, Origami™ modified from *Escherichia coli*; a yeast or *Pichia, Saccharomyces cerevisiae, Kluyveromyces lactis, Hansenula polymorpha* modified from a yeast; an insect cell or High5, SF9 cell modified from an insect cell; a plant cell; a mammalian breast cell, somatic cell.

The fifth aspect of the present invention relates to a composition comprising the bispecific antibody in the form of a heterodimer according to the first aspect, or the isolated polynucleotide according to the second aspect, or the recombinant expression vector according to the third aspect, or the host cell according to the fourth aspect, and a pharmaceutically acceptable carrier.

The sixth aspect of the present invention relates to a method for producing a bispecific antibody in the form of a heterodimer according to the first aspect, which comprises the steps of:

1) expressing the isolated polynucleotide according to the second aspect or the recombinant expression vector according to the third aspect in a host cell respectively;
2) reducing the proteins respectively expressed in the host cell; and
3) mixing thereduced proteins and oxidizing the mixture.

In some embodiments, the host cell is selected from human embryonic kidney cell HEK293 or HEK293T, HEK293F, HEK293E modified from HEK293 cell; hamster ovary cell CHO or CHO-S, CHO-dhfr⁻, CHO/DG44, ExpiCHO modified from CHO cell; *Escherichia coli* or *Escherichia coli* BL21, BL21(DE3), Rosetta™, Origami™ modified from *Escherichia coli*; a yeast or *Pichia, Saccharomyces cerevisiae, Kluyveromyces lactis, Hansenula polymorpha* modified from a yeast; an insect cell or High5, SF9 cell modified from an insect cell; a plant cell; a mammalian breast cell, somatic cell.

In some embodiments, the reduction step comprises 1) performing a reduction reaction in the presence of a reducing agent selected from the group consisting of 2-mercaptoethylamine, dithiothreitol, tris (2-carboxyethyl) phosphine or other chemical derivatives; 2) removing the reducing agent, for example, carrying out the reduction reaction in the presence of dithiothreitol at a concentration of 0.1 mM or higher at 4° C. for at least 3 hours. The limitation of the reducing agent and the conditions of the reduction reaction also applies to other situations involving the use of the reducing agent and the reduction reaction herein.

In some embodiments, the oxidation step is oxidation in the air, and also comprises carrying out an oxidation reaction in the presence of an oxidizing agent selected from the group consisting of L-dehydroascorbic acid or the chemical derivatives thereof. For example, the oxidation reaction is carried out in the presence of L-dehydroascorbic acid at a concentration of 0.5 mM or higher at 4° C. for at least 5 hours.

In some embodiments, the method further comprises the step of separation and purification.

The seventh aspect of the present invention relates to use of the bispecific antibody in the form of a heterodimer according to the first aspect and/or the isolated polynucleotide according to the second aspect and/or the recombinant expression vector according to the third aspect and/or the host cell of the fourth aspect and/or the composition of the fifth aspect in the manufacture of a medicament for preventing and/or treating a disease in a subject.

The eighth aspect of the present invention relates to the bispecific antibody in the form of a heterodimer according to the first aspect and/or the isolated polynucleotide according to the second aspect and/or the recombinant expression vector according to the third aspect and/or the host cell of the fourth aspect and/or the composition of the fifth aspect, for use as a medicament for preventing and/or treating a disease in a subject.

The ninth aspect of the present invention relates to a method for preventing and/or treating a disease, comprising administering the bispecific antibody in the form of a heterodimer according to the first aspect and/or the isolated polynucleotide according to the second aspect and/or the recombinant expression vector according to the third aspect and/or the host cell of the fourth aspect and/or the composition of the fifth aspect to a subject in need thereof.

In some embodiments, the subject is a mammalian, preferably, a human subject.

In some embodiments, the disease is selected from the following tumors: leukemia, lymphoma, myeloma, brain tumor, head and neck squamous cell carcinoma, non-small cell lung cancer, nasopharyngeal carcinoma, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, melanoma, small cell lung cancer, bone cancer.

The invention designs a new anti-PD-L1/anti-CD47 natural antibody structure-like bispecific antibody in the form of a heterodimer. It has natural IgG characteristics and has no heavy chain and light chain mismatch, and is a highly stable anti-PD-L1/anti-CD47 bispecific antibody in the form of a heterodimer. The bispecific antibody prepared by the invention can simultaneously bind to two target molecules PD-L1 and CD47, and when applied to the treatment of complex diseases, it can exert better effects than a single therapeutic agent. At the same time, relative to the combination therapy of multiple drugs, the bispecific antibody as a single therapeutic molecule not only facilitates the use of patients and medical workers, but also simplifies the complex new drug development process.

DETAILED DESCRIPTION

Definition

Figure 1:
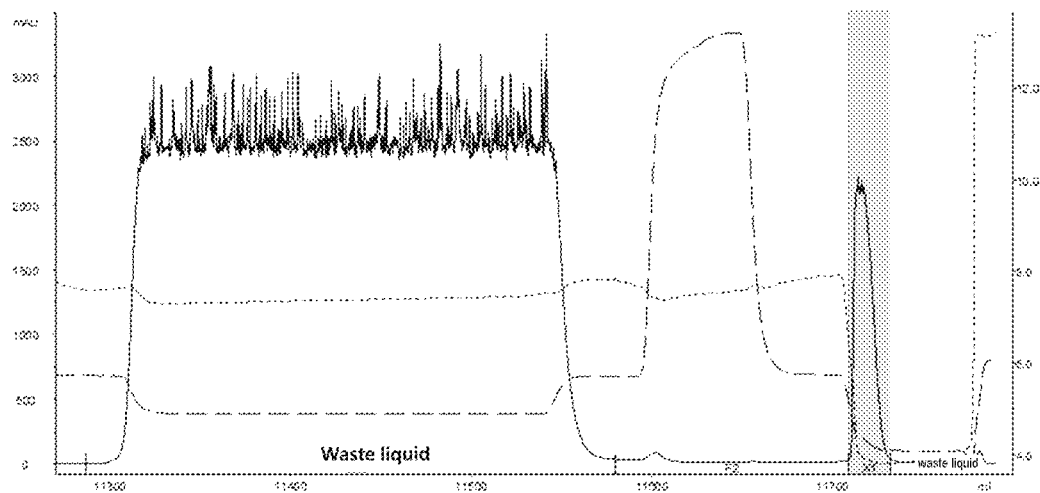
FIG. 1 shows the elution peak chromatogram of an anti-PD-L1-Fc1.

Covalent linkage means that in a bispecific antibody in the form of a heterodimer, the two Fc chains, and either Fc chain and the antigen-binding functional region, are linked to be one molecule by a covalent bond, wherein the Fc chain comprises a first antigen-binding functional region and a second antigen-binding functional region linked via one or more covalent linkages (such as a disulfide bond chain); the first Fc chain and the second Fc chain are respectively linked to an antigen binding functional region via a covalent linkage (such as an imine bond or an amide bond).

The antigen-binding functional region refers to a region that can specifically interact with a target molecule such as an antigen, and its action is highly selective. The sequence that recognizes one target molecule usually cannot recognize the sequences of other molecules. Representative antigen-binding functional regions comprise antibody variable regions, structural variants of antibody variable regions, receptor binding domains, ligand binding domains, or enzyme binding domains.

The linkage between one or more disulfide bond chains means that the first Fc chain and the second Fc chain are linked via one or more disulfide bond chains to form a heterodimer fragment. In the present invention, the one or more disulfide bonds may be formed when the first Fc chain and the second Fc chain, or the first Fc chain and the second Fc chain and the antigen-binding functional regions linked thereto are synthesized in the same cell, or the first Fc chain and the second Fc chain, or the first Fc chain and the second Fc chain and the antigen-binding functional regions linked thereto are synthesized separately in different cells, and then formed by a method of reduction and oxidation in vitro.

The first Fc chain and the second Fc chain refer to a bound fragment formed by a covalent linkage. The covalent linkage comprises a disulfide bond, and each chain comprises at least a part of a constant region of an immunoglobulin heavy chain; and the first Fc chain and the second Fc chain are different in amino acid sequences, including at least one different amino acid. In the first Fc chain and the second Fc chain in the present invention, there is a strong mutual repulsion between the same chains, and there is an attraction between different chains. Therefore, when co-expressed in the cell, the first Fc chain and the second Fc chain, or the first Fc chain and the second Fc chain and the antigen-binding functional regions linked thereto, tend to form a heterodimer. When the first Fc chain and the second Fc chain, or the first Fc chain and the second Fc chain and the antigen-binding functional regions linked thereto are expressed in two host cells respectively, the first Fc chains or the first Fc chain and the antigen-binding functional region linked thereto do not tend to form a homodimer, and the second Fc chains or the second Fc chain and the antigen-binding functional region linked thereto do not tend to form a homodimer. In the present invention, when the first Fc chain and the second Fc chain, or the first Fc chain and the second Fc chain and the antigen-binding functional regions linked thereto are expressed in two host cells respectively, and in the presence of a reducing agent, the proportion of homodimers is less than 50%, that is, the proportion of monomers (one Fc chain or one Fc chain and the antigen-binding functional region linked thereto) is greater than 50%.

Immunoglobulin is a symmetrical structure with four polypeptide chains, two of which are the same heavy chains, which are relatively long and have a larger relative molecular weight, and contain 450 to 550 amino acid residues, and have a relative molecular mass of between 55,000 and 70,000 Da; two of which are the same light chains (L chains), which are relatively short and have a smaller relative molecular weight, and contain about 210 amino acid residues and have a relative molecular mass of about 24,000 Da. A sequence of about 110 amino acids near the N-terminus varies greatly among different immunoglobulin heavy and light chains, and is called a variable region (V region), while the remaining amino acid sequences near the C-terminus are relatively stable and are called constant region (C region). In the heavy chain, the variable region constitutes about ¼ of the length of the heavy chain, and the constant region constitutes about ¾ of the length of the heavy chain. For the five known Igs, IgG (γ), IgA (α), IgD (δ), IgM (μ) and IgE (ε), the first three classes of Igs have three constant regions in the H chain, namely CH1, CH2 and CH3. The H chain of the latter two classes (IgM and IgE) has a VH region and four constant regions, namely CH1 to CH4. The constant region is not only the backbone of the immunoglobulin molecule, but also one of the sites that activate the immune response. Although the examples of the present invention relate to IgG, those skilled in the art know that, if desired, the classes of antibodies of the present invention can be switched by known methods. For example, an antibody of the invention that was originally IgM can be class-switched to an IgG antibody of the invention. In addition, class switching techniques can be used to convert one IgG subclass to another, for example from IgG1 to IgG2. Therefore, the effector function of the antibody of the present invention can be changed to, for example, IgG1, IgG2, IgG3, IgG4, IgD, IgA, IgE, or IgM antibodies by isotype switching for various therapeutic uses. In one example, the antibody of the invention is an IgG1 antibody, such as $IgG1,_\kappa$.

A part of the constant region in the present invention comprises at least the region where the first Fc chain and the second Fc chain interact. For IgG, this region is a part of the amino acids located in the CH3 region, including at least GLN347, TYR349, THR350, LEU351, SER354, ARG355, ASP356, GLU357, LYS360, SER364, THR366, LEU368, LYS370, ASN390, LYS392, THR394, PRO395, VAL397, ASP399, SER400, PHE405, TYR407, LYS409, LYS439.

The first Fc chain and the second Fc chain linked to an antigen-binding functional region via a covalent bond or a linker respectively means that the first Fc chain and the second Fc chain linked to an antigen-binding fragment of an antibody, or a single chain antibody capable of recognizing an antigen, or other antibody fragment variant capable of recognizing an antigen, or a receptor capable of recognizing a ligand, or a ligand capable of recognizing a receptor via a covalent bond or a linker, respectively. The covalent bond is a kind of chemical bonds, in which two or more atoms together use their outer electrons, and under the ideal situations, the status of electronic saturation is achieved, thus forming a relatively stable chemical structure called a chemical bond, or the covalent bond is the interaction between atoms formed by shared electron pair. Atoms of the same element or atoms of different elements may all be linked via the covalent bond. The covalent bond between the first Fc chain and the second Fc chain of the present invention include an amide bond formed by dehydration between an amino group of an amino acid of one molecule and a carboxyl group of an amino acid of another molecule, or an amide bond or an imide bond formed between an aldehyde group of ethylene glycol or polyethylene glycol or other compound or a polymer thereof and an amino group of an amino acid of one molecule, but is not limited thereto. The linker is an amino acid sequence or a compound or a multimer of a compound capable of linking two polypeptide chains via a covalent bond, wherein the amino acid sequence includes, but is not limited to, a small peptide, such as GGGGSGGGGSGGGGS (SEQ ID NO:15), and the amino acid sequence links the first Fc chain or the second Fc chain and a single chain antibody capable of recognizing an antigen, or other antibody fragment structural variant capable of recognizing an antigen via an amide bond.

The first Fc chain and the second Fc chain have a tendency to undergo heterodimeric formation and no tendency to undergo homodimeric formation, which means that in the first Fc chain and the second Fc chain, a strong repulsive force exists between the same polypeptide chains and an attractive force exists between the different polypeptide chains, and therefore, the first Fc chain and the second Fc chain, or the first Fc chain and the second Fc chain and the antigen-binding functional regions linked thereto have a tendency to undergo heterodimeric formation, when co-expressed in a cell. When the first Fc chain and the second Fc chain, or the first Fc chain and the second Fc chain and the antigen-binding functional regions linked thereto are expressed in two host cells, respectively, the first Fc chains, or the first Fc chain and the antigen-binding functional region linked thereto have no tendency to undergo homodimeric formation, and the second Fc chains, or the second Fc chain and the antigen-binding functional region linked thereto also have no tendency to undergo homodimeric formation.

The Kabat EU numbering system means that Kabat assigns a number to each amino acid in an antibody sequence, and this method of assigning the number of each residue has become standard in the field. The Kabat's method is extendible to other antibodies not included in his reach by aligning a target antibody with one of the consensus sequences identified by Kabat based on conserved amino acids.

An Fc domain refers to a fragment crystallizable (Fc) and corresponds to CH2 and CH3 structural domains of Ig, and is a site where an interaction between Ig and an effector molecule or a cell occurs.

IgG is an abbreviation for immunoglobulin G (IgG), and is the main component of antibody in the serum. Human IgG has four subclasses of IgG1, IgG2, IgG3, and IgG4 based on antigenic differences in r chains in the IgG molecule.

A half antibody molecule refers to a structure formed by one heavy chain and one light chain of an antibody, wherein the heavy chain and the light chain may be linked via a covalent bond, or has a monovalent antibody structure recognizing an antigen, which may be formed without a covalent bond.

Fab fragment is a molecule-recognizing sequence, and a fragment of antigen binding (Fab), and corresponds to two arms of an antibody molecule, each consisting of a complete light chain and VH and CH1 structural domains of a heavy chain. scFv is a molecule-recognizing sequence, and is a structural isomer of an antibody fragment obtained by genetic engineering of a light chain variable region and a heavy chain variable region of an antibody. An extracellular domain of a membrane receptor is a molecule-recognizing sequence, and the membrane receptor usually includes an extracellular region that is located outside the cell and recognizes and binds to the corresponding antigen or ligand, a transmembrane region that anchors the receptor onto the cell surface, and an intracellular region that has intracellular kinase activity or a signaling pathway. The ligand of the cell membrane receptor refers to a protein, a small peptide, or a compound that may be recognized and bound by the extracellular region of the membrane receptor. Cytokines are low-molecular weight soluble proteins that are produced by various types of cells induced by immunogens, mitogens, or other stimulants, and have various functions such as regulating innate immunity and adaptive immunity, hematopoiesis, cell growth, APSC multipotent cell and damage tissue repair, etc. Cytokines may be classified into interleukins, interferons, tumor necrosis factor superfamilies, colony stimulating factors, chemotactic factors, growth factors, etc. A protein expression tag means an amino acid sequence added at the N-terminus or C-terminus of a target protein, and may be small peptides or long amino acids. Addition of the tag may be advantageous for correct folding of proteins, protein isolation and purification, and intracellular protein degradation. Tags frequently used may include HA, SUMO, His, GST, GFP, and Flag, but are not limited thereto.

There is no limitation to the antibodies applicable to the bispecific antibody in the form of a heterodimer of the present invention. Preferably, the antibodies already used in the art for the treatment and/or prevention of diseases may be applied to the present invention.

The bispecific antibody in the form of a heterodimer of the present invention may have one or more substitutions, deletions, additions, and/or insertions. For example, some amino acids may be substituted for other amino acids in the structure of the protein without significant loss of the ability to bind to other polypeptides (e.g., antigens) or cells. Since the binding ability and properties of the protein determine the biological functional activity of the protein, substitution of some amino acids on the protein sequence may cause no significant loss of its biological usefulness or activity.

In many cases, polypeptide variants include one or more conservative substitutions. The "conservative substitution" means that amino acids therein are replaced by other amino acids having similar properties, such that those skilled in the art of peptide chemistry would expect a secondary structure and hydrophilic nature of the polypeptide to be substantially unchanged.

Amino acid substitutions are generally based on relative similarity of amino acid side-chain substituents such as hydrophobicity, hydrophilicity, charge, size, etc. Exemplary substitutions that take various characteristics described above into consideration are well known to those skilled in the art and include arginine and lysine; glutamic acid and aspartic acid; serine and threonine; glutamine and asparagine; and valine, leucine, and isoleucine.

As used herein, the term "identity" has the meaning commonly known in the art, and those skilled in the art also are familiar with the rules and criteria for determining identity between different sequences, and the identity refers to the percentage of homology between residues of a polynucleotide or polypeptide sequence variant and residues of a non-variant sequence after aligning the sequences and introducing gaps (if necessary, to achieve the maximum % homology). In the present invention, when the definition of identity is satisfied, it is also required that the obtained variant sequence has the biological activities possessed by the parent sequence. Methods and means for screening variant sequences using the above activities are well known to those skilled in the art. Such variant sequences may be readily obtained by those skilled in the art from the teachings herein. In a specific embodiment, the polynucleotide and polypeptide variants have at least about 70%, at least about 75%, at least about 80%, at least about 90%, at least about 95%, at least about 98%, or at least about 99%, or at least about 99.1%, 99.2%, 99.3%, 99.4%, 99.5%, 99.6%, 99.7%, 99.8% or 99.9% polynucleotide or polypeptide identity with the polynucleotide or polypeptide described herein. Due to redundancy of the genetic codes, variants of these sequences encoding the same amino acid sequence will exist.

Another embodiment of the present invention provides a polynucleotide composition capable of hybridizing to the polynucleotide sequence provided by the present invention or a fragment thereof or a complementary sequence thereof under moderately to highly stringent conditions. Hybridization techniques are well known in the art of molecular biology. For the purposes of explanation, suitable moderately stringent conditions for testing hybridization of the polynucleotide of the present invention to another polynucleotide may include pre-washing with a solution of 5×SSC, 0.5% SDS, 1.0 mM EDTA (pH 8.0); performing hybridization in 5×SSC at 50° C. to 60° C. overnight; and washing twice with 2×, 0.5× and 0.2×SSC containing 0.1% SDS for 20 minutes at 65° C., respectively. Those skilled in the art understand that the stringency of hybridization may be readily manipulated, for example, by varying the salt content of the hybridization solution and/or the hybridization temperature. For example, in another embodiment, suitable highly stringent hybridization conditions include the conditions described above, except for increasing the hybridization temperature, for example, to 60° C. to 65° C. or 65° C. to 70° C.

The host cell of the present invention may be any cell which may be used in foreign gene expression, and include E. coli, yeast cells, insect cells, plant cells, and mammalian cells, but is not limited thereto.

The vector of the present invention includes a vector which may replicate in any type of cells or organisms, and include, for example, plasmids, bacteriophages, cosmids, and minichromosomes. In some embodiments, the vector including the polynucleotide of the present invention is a vector suitable for propagation or replication of a polynucleotide, or a vector suitable for expression of the polypeptide of the present invention. Such vectors are known in the art and are commercially available.

The "vector" may include a shuttle vector and an expression vector. Generally, a plasmid construct may also include an origin of replication (e.g., ColE1 origin of replication) and a selectable marker (e.g., ampicillin or tetracycline resistance) which are for plasmid replication and selection in bacteria, respectively. The "expression vector" refers to a vector including a control sequence or a regulatory element which is required for expression of the antibody of the present invention, including antibody fragments, in bacterial or eukaryotic cells.

The vector of the present invention may be any vector used for foreign gene expression, and may include, but is not limited to, a plasmid vector, wherein the plasmid vector includes at least an origin of replication, a promoter, a gene of interest, a multiple cloning site, a selection marker gene. Preferably, the vector of the present invention includes, but is not limited to, a plasmid vector obtained by modifying pcDNA, such as X0GC vector.

The subject of the present invention may include birds, reptiles, mammals, etc. The mammal includes a rodent, a primate. Preferably, the primate includes a human.

The scope of the diseases involved in the present invention includes, but is not limited to, tumors. Preferably, the tumors may include leukemia, lymphoma, myeloma, brain tumor, head and neck squamous cell carcinoma, non-small cell lung cancer, nasopharyngeal carcinoma, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, melanoma, small cell lung cancer, bone cancer.

A pharmaceutically acceptable carrier means a pharmaceutical carrier which is commonly used in the pharmaceutical art, for example, diluents, excipients, water, etc., fillers such as starch, sucrose, lactose, microcrystalline cellulose, etc.; binders such as cellulose derivatives, alginates, gelatin and polyvinylpyrrolidone; wetting agents such as glycerin; disintegrating agents such as sodium carboxymethyl starch, hydroxypropyl cellulose, croscarmellose, agar, calcium carbonate, sodium hydrogencarbonate, etc.; absorption enhancers such as quaternary ammonium compounds; surfactants such as cetanol, sodium lauryl sulfate, etc.; adsorption carriers such as kaolinite, bentonite, etc.; lubricants such as talc, calcium and magnesium stearate, micronized silica gel, polyethylene glycol, etc. In addition, other additives such as flavoring agents, sweeteners, etc. may be added to the composition.

In some embodiments, the present invention relates to the following technical solutions.

Technical solution 1. A bispecific antibody in the form of a heterodimer, which comprises a first antigen-binding functional region that can specifically bind to PD-L1 and a second antigen-binding functional region that can specifically bind to CD47, wherein the bispecific antibody comprises a first Fc chain and a second Fc chain linked via one or more disulfide bond chains, and the first Fc chain and the second Fc chain are linked to a PD-L1 antigen binding functional region and a CD47 antigen binding functional region respectively via a covalent bond or a linker, or the first Fc chain and the second Fc chain are linked to a CD47 antigen binding functional region and a PD-L1 antigen binding functional region respectively via a covalent bond or a linker; and the first Fc chain and the second Fc chain comprise 5 amino acid substitutions at the following positions:

1) amino acid substitutions at positions 366 and 399 in the first Fc chain, and amino acid substitutions at positions 351, 407, and 409 in the second Fc chain; or 2) amino acid substitutions at positions 366 and 409 in the first Fc chain, and amino acid substitutions at positions 351, 399, and 407 in the second Fc chain;

the first Fc chain and the second Fc chain comprising the above-mentioned amino acid substitutions tend to form a heterodimer with each other rather than each forms a homodimer, wherein the amino acid positions are numbered according to the Kabat EU index numbering system.

Technical solution 2. The bispecific antibody in the form of a heterodimer according to technical solution 1, wherein the amino acid substitutions of the first Fc chain and the second Fc chain are as follows:

a) substitution by glycine, tyrosine, valine, proline, aspartic acid, glutamic acid, lysine or tryptophan at position 351;

b) substitution by leucine, proline, tryptophan or valine at position 366;

c) substitution by cysteine, asparagine, isoleucine, glycine, arginine, threonine or alanine at position 399;

d) substitution by leucine, alanine, proline, phenylalanine, threonine or histidine at position 407; and e) substitution by cysteine, proline, serine, phenylalanine, valine, glutamine or arginine at position 409.

Technical solution 3. The bispecific antibody in the form of a heterodimer according to technical solution 1 or 2, wherein the amino acid substitutions comprise:

a) T366L and D399R substitutions in the first Fc chain, and L351E, Y407L and K409V substitutions in the second Fc chain;

b) T366L and D399C substitutions in the first Fc chain, and L351G, Y407L and K409C substitutions in the second Fc chain;

c) T366L and D399C substitutions in the first Fc chain, and L351Y, Y407A and K409P substitutions in the second Fc chain;

d) T366P and D399N substitutions in the first Fc chain, and L351V, Y407P and K409S substitutions in the second Fc chain;

e) T366W and D399G substitutions in the first Fc chain, and L351D, Y407P and K409S substitutions in the second Fc chain;

f) T366P and D399I substitutions in the first Fc chain, and L351P, Y407F and K409F substitutions in the second Fc chain;

g) T366V and D399T substitutions in the first Fc chain, and L351K, Y407T and K409Q substitutions in the second Fc chain;

h) T366L and D399A substitutions in the first Fc chain, and L351W, Y407H, and K409R substitutions in the second Fc chain.

Technical solution 4. The bispecific antibody in the form of a heterodimer according to any one of technical solutions 1-3, wherein the amino acid substitutions comprise:

a) T366L and K409V substitutions in the first Fc chain, and L351E, Y407L and D399R substitutions in the second Fc chain;

b) T366L and K409C substitutions in the first Fc chain, and L351G, Y407L and D399C substitutions in the second Fc chain;

c) T366L and K409P substitutions in the first Fc chain, and L351Y, Y407A and D399C substitutions in the second Fc chain;

d) T366P and K409S substitutions in the first Fc chain, and L351V, Y407P and D399N substitutions in the second Fc chain;

e) T366W and K409S substitutions in the first Fc chain, and L351D, Y407P and D399G substitutions in the second Fc chain;

f) T366P and K409F substitutions in the first Fc chain, and L351P, Y407F and D399I substitutions in the second Fc chain;

g) T366V and K409Q substitutions in the first Fc chain, and L351K, Y407T and D399T substitutions in the second Fc chain;

h) T366L and K409R substitutions in the first Fc chain, and L351W, Y407H and D399A substitutions in the second Fc chain.

Technical solution 5. The bispecific antibody in the form of a heterodimer according to technical solution 1, wherein the amino acids of the first Fc chain are substituted by T366L and D399R, and the amino acids of the second Fc chain are substituted by L351E, Y407L and K409V.

Technical solution 6. The bispecific antibody in the form of a heterodimer according to any one of technical solutions 1-5, wherein the Fc chain is derived from IgG.

Technical solution 7. The bispecific antibody in the form of a heterodimer according to any one of technical solutions 1-6, wherein the PD-L1 and CD47 antigen binding functional regions are Fab fragments or scFv fragments.

Technical solution 8. The bispecific antibody in the form of a heterodimer according to any one of technical solutions 1-7, wherein the PD-L1 and CD47 antigen binding functional regions are both Fab fragments.

Technical solution 9. The bispecific antibody in the form of a heterodimer according to technical solutions 1-7, wherein one of the PD-L1 and CD47 antigen binding functional regions is a Fab fragment, and the other is a scFv.

Technical solution 10. The bispecific antibody in the form of a heterodimer according to any one of technical solutions 7-9, wherein the Fab fragment comprises different first heavy chain variable region and second heavy chain variable region, and different first light chain variable region and second light chain variable region.

Technical solution 11. The bispecific antibody in the form of a heterodimer according to any one of technical solutions 1-10, wherein when the first Fc chain and PD-L1 antigen binding functional region linked thereto, and the second Fc chain and the CD47 antigen binding functional region linked thereto, or the first Fc chain and CD47 antigen binding functional region linked thereto, and the second Fc chain and the PD-L1 antigen binding functional region linked thereto, are present alone or together with a reducing agent, form less than 50% of homodimers by weight.

Technical solution 12. The bispecific antibody in the form of a heterodimer according to any one of technical solutions 1-11, wherein the amino acid sequence of the bispecific antibody is selected from SEQ ID NOs: 2, 4, 6, 8, 10, 12 and 14.

Technical solution 13. An isolated polynucleotide encoding a bispecific antibody in the form of a heterodimer according to any one of technical solutions 1-12.

Technical solution 14. The isolated polynucleotide according to technical solution 13, having the sequence selected from: SEQ ID NOs: 1, 3, 5, 7, 9, 11 and 13.

Technical solution 15. A recombinant expression vector comprising the isolated polynucleotide according to technical solution 13 or 14.

Technical solution 16. The recombinant expression vector according to technical solution 15, wherein the expression vector is a plasmid vector X0GC modified from pCDNA.

Technical solution 17. A host cell comprising the isolated to polynucleotide according to technical solution 13 or 14, or the recombinant expression vector according to technical solution 15 or 16.

Technical solution 18. The host cell according to technical solution 17, which is selected from human embryonic kidney cell HEK293 or HEK293T, HEK293E, HEK293F modified from HEK293 cell; hamster ovary cell CHO or CHO-S, CHO-dhfr⁻, CHO/DG44, ExpiCHO modified from CHO cell; *Escherichia coli* or *Escherichia coli* BL21, BL21(DE3), Rosetta™, Origami™ modified from *Escherichia coli*; a yeast or *Pichia, Saccharomyces cerevisiae, Kluyveromyces lactis, Hansenula polymorpha* modified from a yeast; an insect cell or High5, SF9 cell modified from an insect cell; a plant cell; a mammalian breast cell, somatic cell.

Technical solution 19. A composition comprising the bispecific antibody in the form of a heterodimer according to any one of technical solutions 1-12 or the isolated polynucleotide according to technical solution 13 or 14 or the recombinant expression vector according to technical solution 15 or 16 or the host cell according to technical solution 17 or 18, and a pharmaceutically acceptable carrier.

Technical solution 20. A method for producing a bispecific antibody in the form of a heterodimer according to any one of technical solutions 1-12, which comprises the steps of:

1) expressing the isolated polynucleotide according to technical solution 13 or 14 or the recombinant expression vector according to technical solution 15 or 16 in a host cell respectively;

2) reducing the proteins respectively expressed in the host cell; and 3) mixing thereduced proteins and oxidizing the mixture.

Technical solution 21. The method according to technical solution 20, wherein the host cell is selected from human embryonic kidney cell HEK293 or HEK293T, HEK293F, HEK293E modified from HEK293 cell; hamster ovary cell CHO or CHO-S, CHO-dhfr⁻, CHO/DG44, ExpiCHO modified from CHO cell; *Escherichia coli* or *Escherichia coli* BL21, BL21(DE3), Rosetta™, Origami™ modified from *Escherichia coli*; a yeast or *Pichia, Saccharomyces cerevisiae, Kluyveromyces lactis, Hansenula polymorpha* modified from a yeast; an insect cell or High5, SF9 cell modified from an insect cell; a plant cell; a mammalian breast cell, somatic cell.

Technical solution 22. The method according to technical solution 20 or 21, wherein the reducing step comprises 1) adding a reducing agent selected from the group consisting of 2-mercaptoethylamine, dithiothreitol, tris(2-carboxyethyl)phosphine or other chemical derivatives; 2) carrying out a reduction reaction in the presence of dithiothreitol at a concentration of 0.1 mM or higher at 4° C. for at least 3 hours, 3) removing the reducing agent, such as by desalting.

Technical solution 23. The method according to any one of technical solutions 20-22, wherein the oxidizing step comprises 1) oxidizing in the air, and also comprises adding an oxidizing agent selected from the group consisting of L-dehydroascorbic acid or other chemical derivatives, 2) carrying out the oxidation reaction in the presence of L-dehydroascorbic acid at a concentration of 0.5 mM or higher at 4° C. for at least 5 hours.

Technical solution 24. The method according to any one of technical solutions 20-23, further comprising a step of separation and purification.

Technical Solution 25. Use of the bispecific antibody in the form of a heterodimer according to any one of technical solutions 1-12 and/or the isolated polynucleotide according to technical solution 13 or 14 and/or the recombinant expression vector according to technical solution 15 or 16 and/or the host cell according to technical solution 17 or 18 and/or the composition according to technical solution 19 in the manufacture of a medicament for preventing and/or treating a disease in a subject.

Technical solution 26. The bispecific antibody in the form of a heterodimer according to any one of technical solutions 1-12 and/or the isolated polynucleotide according to technical solution 13 or 14 and/or the recombinant expression vector according to technical solution 15 or 16 and/or the host cell according to technical solution 17 or 18 and/or the composition according to technical solution 19, for use as a medicament for preventing and/or treating a disease in a subject.

Technical solution 27. A method for preventing and/or treating a disease, comprising administering the bispecific antibody in the form of a heterodimer according to any one of technical solutions 1-12 and/or the isolated polynucleotide according to technical solution 13 or 14 and/or the recombinant expression vector according to technical solution 15 or 16 and/or the host cell according to technical solution 17 or 18 and/or the composition according to technical solution 19 to a subject in need thereof.

Technical solution 28. The use according to technical solution 25, the bispecific antibody in the form of a heterodimer, the isolated polynucleotide, the recombinant expression vector, the host cell or the composition according to technical solution 26, or the method according to technical solution 27, wherein the subject is a mammalian, preferably, a human subject.

Technical solution 29. The use according to technical solution 25, the bispecific antibody in the form of a heterodimer, the isolated polynucleotide, the recombinant expression vector, the host cell or the composition according to technical solution 26, or the method according to technical solution 27, wherein the disease is selected from the following tumors: leukemia, lymphoma, myeloma, brain tumor, head and neck squamous cell carcinoma, non-small cell lung cancer, nasopharyngeal carcinoma, esophageal cancer, gastric cancer, pancreatic cancer, gallbladder cancer, liver cancer, colorectal cancer, breast cancer, ovarian cancer, cervical cancer, endometrial cancer, uterine sarcoma, prostate cancer, bladder cancer, renal cell carcinoma, melanoma, small cell lung cancer, bone cancer.

Hereinafter, the present invention will be described in more detail with reference to the following non-limiting examples. It will be understood by those skilled in the art that various modifications may be made therein without departing from the spirit of the present invention, and the modifications are also included in the scope of the present invention.

The following experimental methods are all common methods unless otherwise specified, and the experimental materials used may be also easily obtained from commercial companies unless otherwise specified. The various antibodies used in the following Examples of the present invention are all standard antibodies obtained from the commercial route.

Example 1: Construction of Vector of Anti-PD-L1/Anti-CD47 Heterodimeric Antibody Molecule X0GC expression vectors comprising heavy chain and light chain of anti-human PD-L1 antibody were constructed, respectively, wherein the sequence of the variable region of the antibody was derived at the World Wide Web at imgt.org/mAb-DB/mAbcard?AbId=526, and the heavy chain constant region was human IgG1 (Fc1, in which N297A mutation was introduced to eliminate ADCC/CDC effect). The nucleotide sequence of the light chain variable region is shown in SEQ ID NO. 1 and the amino acid sequence thereof is shown in SEQ ID NO. 2; the nucleotide sequence of the light chain constant region is shown in SEQ ID NO. 3 and the amino acid sequence thereof is shown in SEQ ID NO. 4; the nucleotide sequence of the heavy chain variable region is shown in SEQ ID NO. 5 and the amino acid sequence thereof is shown in SEQ ID NO. 6; the nucleotide sequence of the heavy chain constant region is shown in SEQ ID NO. 7 and the amino acid sequence thereof is shown in SEQ ID NO. 8. The light chain variable region and the light chain constant region, and the heavy chain variable region and the heavy chain constant region were amplified by PCR, respectively. In all PCR reactions of the present application, Phusion® (DNA polymerase) high-fidelity DNA polymerase (F-530L) of NEB, Inc. was used. PCR primers were designed commonly according to the principle of base complementation and the need for enzymatic digestion sites. The reaction system each consisted of 8.9 µl of H$_2$O, 4 µl of 5×Phusion® (DNA polymerase) high-fidelity DNA polymerase buffer, 4 µl of 1 mM dNTP, 1 µl of forward primer, 1 µl of reverse primer, 0.1 µl of Phusion® (DNA polymerase) high-fidelity DNA polymerase, and 1 µl of the template. PCR products of the variable region and the constant region were electrophoresed on 1.5% agarose gel, and corresponding fragments were recovered using a DNA recovery kit (Promega, A9282, the same below). The recovered variable region fragment and constant region fragment were used as templates and a forward primer of the variable region and a reverse primer of the constant region were used to perform another cycle of PCR. Corresponding fragments were recovered again to obtain full length fragments of the light chain or the heavy chain. X0GC vector and the full length fragments were enzymatically digested with EcoRI (NEB, Cat. No. R3101L) and HindIII (NEB, Cat. No. R3104L). The enzymatic digestion system consisted of 2 µl of 10×buffer 3, 0.5 µl of EcoRI and HindIII each, 3 µl of full length fragments recovered from the gel, and 14.5 µl of H$_2$O. The enzymatic digestion system was allowed to react at 37° C. for three hours. The enzymatically digested products were ligated using T4DNA ligase (NEB, Cat. No. M0202V) (the same below), and the reaction system consisted of 2 µl of 10× ligase buffer, 0.5 µl of ligase, 3 µl of the full length fragments recovered from the gel, 3 µl of the X0GC vector recovered from the gel, and 11.5 µl of H$_2$O. Ligation was carried out at room temperature for 12 hours. The ligation product was transformed into *E. coli* competent cell DH5α (Tiangen, CB104, the same below). The X0GC expression vectors of antibody heavy chain and light chain were obtained in order to express the antibody heavy chain (Fc1) and light chain in eukaryotic cells, respectively.

In the present invention, X0GC expression vectors comprising heavy chain and light chain of anti-human CD47 antibody were constructed, respectively, wherein the sequence of the variable region of the antibody was derived from WO2016109415A1. The nucleotide sequence of the light chain variable region is shown in SEQ ID NO. 9 and the amino acid sequence thereof is shown in SEQ ID NO. 10; the nucleotide sequence of the light chain constant region is shown in SEQ ID NO. 3 and the amino acid sequence thereof is shown in SEQ ID NO. 4; the nucleotide sequence of the heavy chain variable region is shown in SEQ ID NO. 11 and the amino acid sequence thereof is shown in SEQ ID NO. 12; the nucleotide sequence of the heavy chain constant region is shown in SEQ ID NO. 13 and the amino acid sequence thereof is shown in SEQ ID NO. 14. The X0GC expression vectors of antibody heavy chain and light chain were obtained in order to express the antibody heavy chain (Fc2) and light chain in eukaryotic cells, respectively.

Example 2: Expression of Anti-PD-L1/Anti-CD47 Heterodimeric Antibody Molecule The expression vectors comprising the heavy chain and the light chain of anti-human PD-L1 antibody were transfected into 293F cells (FreeStyle™ 293-F Cells, Cat. No. R79007, Invitrogen), respectively, and the expression vectors comprising the heavy chain and the light chain of anti-human CD47 antibody were also transfected into 293F cells, respectively. One day before transfection, cells were seeded. On the day of transfection, cells were collected by centrifugation, and resuspended in fresh FreeStyle™ 293 expression medium (Cat. No. 12338001, Gibco) at a cell density of $200*10^5$ cells/mL. The plasmids were added according to the transfection volume to the final concentration of 36.67 µg/mL, and the medium was gently mixed to homogeneous. Then, linear PEI (polyethylene imine, linear, M.W. 25000, Cat. No. 43896, Alfa Aesar) was added to the final concentration of 55 µg/mL, and the medium was gently mixed to homogeneous. Then, the mixture was placed in an incubator, and incubated on a 120 rpm shaker at 37° C. for 1 hour. Then, 19 times transfection volume of fresh medium was added thereto. Incubation was continuously performed on a 120 rpm shaker at 37° C. Culture supernatant of the cells transfected for 5 to 6 days were collected by centrifugation.

The expression level was determined by ELISA. Before purification by chromatography column, the precipitate was removed by filtering through a 0.2 µm filter. This step was performed at 4° C.

Figure 2:
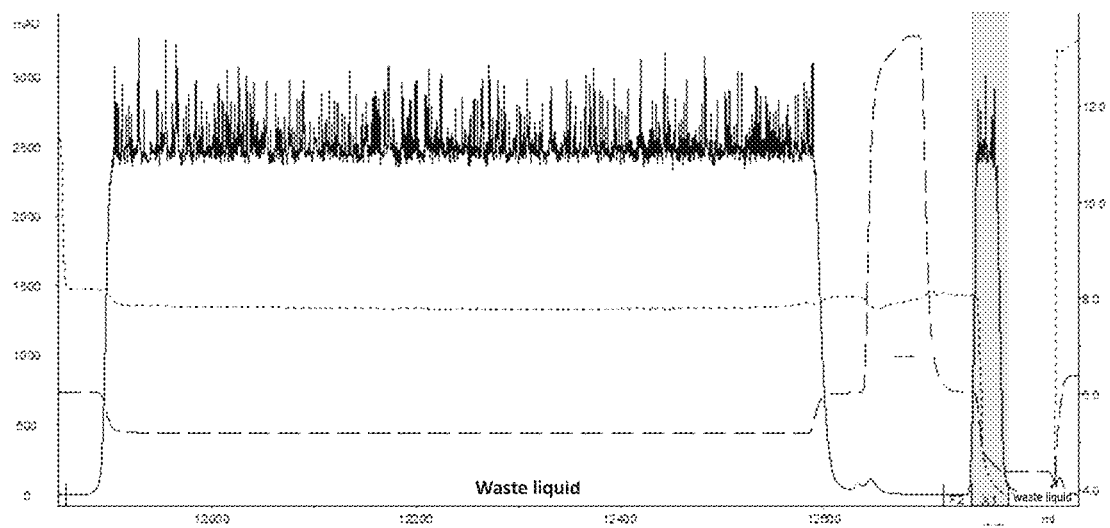
FIG. 2 shows the elution peak chromatogram of an anti-CD47-Fc2.

Example 3. Purification of Expression Product of Anti-PD-L1/Anti-CD47 Heterodimeric Antibody Molecule Purification was performed at 4° C. using AKTA® (liquid chromatography) explorer type 100 protein purification system (GE Healthcare) and affinity chromatography column rProtein A Sepharose® (a crosslinked, beaded-form of agarose) Fast Flow (16 mm I.D., 22 ml, GE Healthcare). Firstly, a mobile phase A (20 mM sodium phosphate buffer, 150 mM sodium chloride, pH 7.4) was used to equilibrate the chromatography column. After a baseline was stabilized, the supernatant of the above treated cells was loaded at a flow rate of 5 mL/min. After loading the sample, equilibration was performed using the mobile phase A. The samples were the anti-PD-L1 expression product and the anti-CD47 expression product, respectively. Thereafter, a mobile phase B1 (mobile phase A containing 0.5 M arginine) was used to elute 5 column volumes; Then, a mobile phase B2 (100 mM citric acid, pH 3.0) was used to elute 5 column volumes to collect an elution peak, i.e., a peak of the protein of interest. The flow rate during the above washing steps was all 5 mL/min. The chromatogram of the elution peak of anti-PD-L1-Fc1 is shown in FIG. 1, and the elution peak of anti-CD47-Fc2 is shown in FIG. 2. The indicated elution peak (grey area shown in the figure) was collected and pH was adjusted to 5.0 by dropwise addition of 1 M sodium acetate solution.

Figure 3:
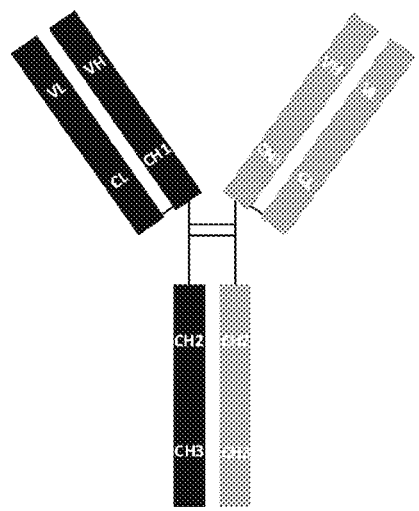
FIG. 3 shows the structure of an anti-PD-L1/anti-CD47 heterodimeric antibody molecule.

Example 4. Preparation and Purification of Anti-PD-L1/Anti-CD47 Heterodimeric Antibody Molecule The structure of the anti-PD-L1/anti-CD47 heterodimeric antibody molecule is as illustrated in FIG. 3.

Figure 4:
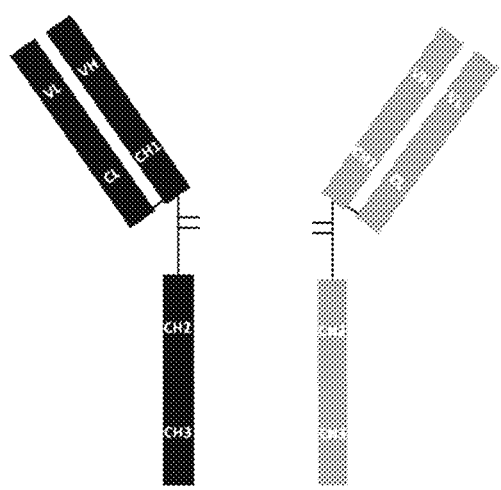
FIG. 4 shows the structure of a half-antibody molecule of one heavy chain and one light chain.
Figure 5:
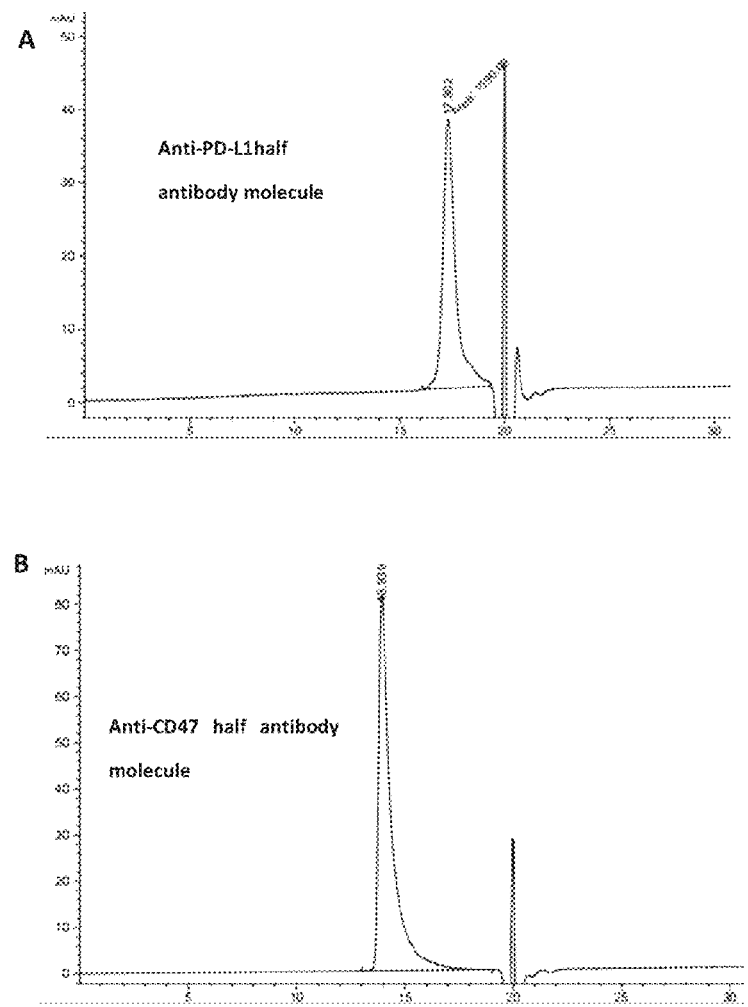
FIG. 5 shows the results of SEC-HPLC analysis of a half-antibody molecule of one heavy chain and one light chain. Panel A and panel B show the results of an anti-PD-L1 half-antibody molecule and an anti-CD47 half-antibody molecule, respectively.

The product obtained by the above-described rProtein A Sepharose® (a crosslinked, beaded-form of agarose) Fast Flow (16 mm I.D., 22 mL, GE Healthcare) method was subjected to in vitro recombination to obtain a heterodimer. Firstly, the above purified and collected protein solution was concentrated by ultrafiltration through an ultrafiltration concentrating tube (nominal molecular weight cut-off of 10 kDa), and the solution was replaced by phosphate buffer saline (PBS) (pH=7.4). The solutions of the obtained anti-PD-L1 and anti-CD47 purification products were respectively adjusted to 1 mg/mL by adding PBS, and 1/200 times the final volume of 1 M DTT was added (the final concentrations of DTT were 0.1 mM, 0.5 mM, 1 mM, 2 mM, 5 mM, 10 mM, 20 mM, respectively). The reduction was carried out at 4° C. (3 hours to 8 hours), and the disulfide bonds were opened through the reduction process. The disulfide bonds in the hinge regions of antibody homodimeric molecules contained in the anti-PD-L1 and anti-CD47 products were also opened, thereby forming a half-antibody molecule containing one heavy chain and one light chain, whose structure is as illustrated in FIG. 4. The reduced sample was analyzed by SEC-HPLC (TOSOH, TSKgel® (HPLC column) superSW3000) comprising 1 mM DTT reducing agent in the mobile phase buffer. The results are shown in FIG. 5. The ratio of anti-PD-L1 and anti-CD47 homodimers was all less than 10%, while the ratio of the half antibody molecules was all more than 90%.

Thereafter, the reduced anti-PD-L1 and anti-CD47 half antibody molecules were mixed in equal molar ratio, and recombination reaction was carried out at 4° C. for 0.5-24 hours. During recombination, a heterodimeric bispecific antibody comprising both the anti-PD-L1 and anti-CD47 half antibody molecules was formed via non-covalent interaction between CH2 and CH3 of the anti-PD-L1 and anti-CD47 half antibody molecules. Then, the protein solution was concentrated by ultrafiltration through an ultrafiltration concentrating tube (nominal molecular weight cut-off of 10 kDa), and the solution was replaced by phosphate solution (PBS, pH=7.4) to stop the reduction. The solution was subjected to oxidation in the air or with an oxidizing agent to allow formation of disulfide bonds of the heterodimeric bispecific antibody. The oxidation conditions included: The sample was placed in the air for 1 day, 3 days, 4 days. 100 mM L-dehydroascorbic acid as the oxidizing agent was added (the final concentration of the protein was 1 mg/mL and the final concentrations of the oxidizing agent were 0.5 mM, 1 mM, 5 mM, 10 mM), and the oxidation was performed at 4° C. for 24 hours.

Figure 6:
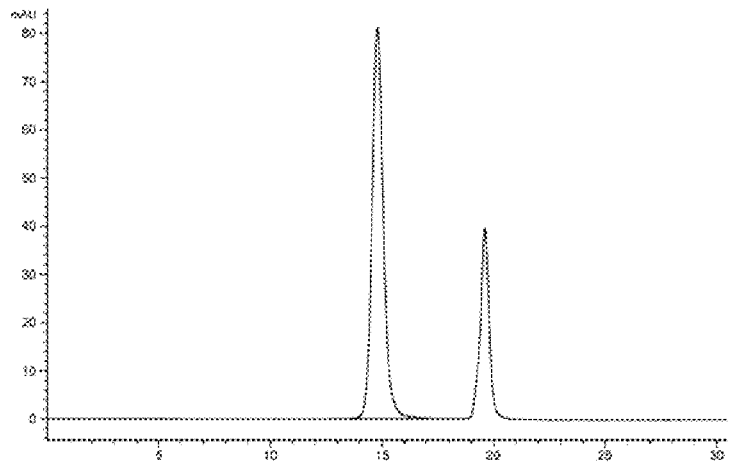
FIG. 6 shows the results of SEC-HPLC analysis of an anti-PD-L1/anti-CD47 heterodimeric antibody molecule.
Figure 7:
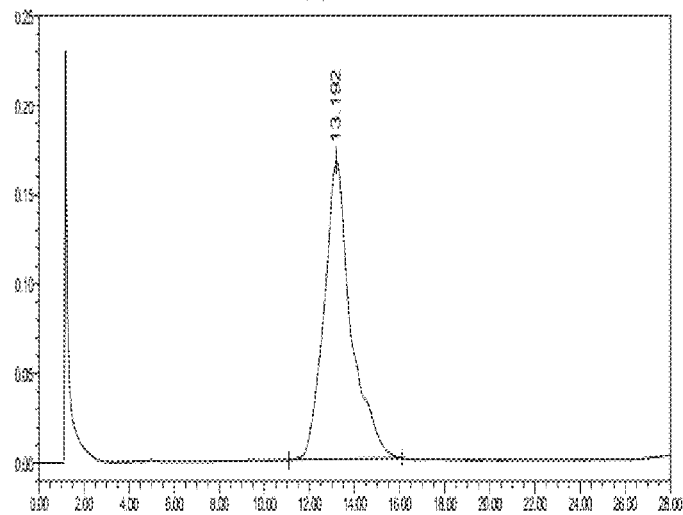
FIG. 7 shows the results of RPC analysis of an anti-PD-L1/anti-CD47 heterodimeric antibody molecule.
Figure 8:
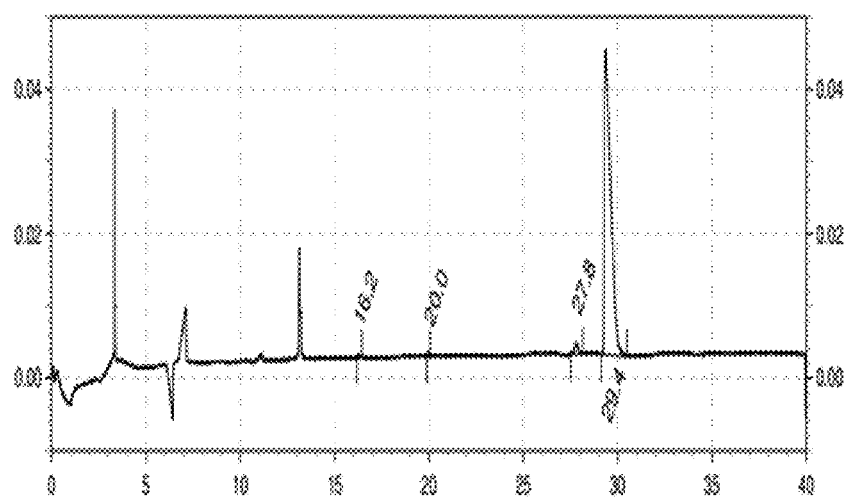
FIG. 8 shows the results of CE analysis of an anti-PD-L1/anti-CD47 heterodimeric antibody molecule.

The anti-PD-L1/anti-CD47 heterodimer molecule obtained by the reduction/oxidation of the above-described anti-PD-L1 and anti-CD47 expression products were concentrated by ultrafiltration through an ultrafiltration concentrating tube (nominal molecular weight cut-off of 10 kDa), and the solution was replaced by a sodium phosphate buffer solution, pH 5.8. Purification was performed at 4° C. using AKTA® (liquid chromatography) explorer type 100 protein purification system (GE Healthcare) and ion chromatography column Source 15S (16 mm I.D., 17 mL, GE Healthcare). Firstly, a mobile phase A (10 mM sodium phosphate, pH 7.0) was used to equilibrate the chromatography column. After a baseline was stabilized, the above-treated protein solution was loaded at a flow rate of 3 mL/min. After loading the sample, equilibration was performed using the mobile phase A. Thereafter, 20 column volumes (0% B-100% B, 170 min, flow rate 2 mL/min) were washed with a gradient of A (10 mM sodium phosphate, pH 5.8) to B (10 mM sodium phosphate, pH 5.8). The elution main peak was collected, and the collected protein solution was concentrated by ultrafiltration through an ultrafiltration concentrating tube (nominal molecular weight cut-off of 10 kDa). The solution was replaced by a phosphate solution (PBS, pH=7.4), and filtered and sterilized, and then stored at 4° C. The purity of the purified product was analyzed by SEC-HPLC method, and the results are shown in FIG. 6. The purity was 99.3%. As a result of RPC-HPLC (Thermo Fisher, MAbPac RP) analysis, the purity was 100%, as shown in FIG. 7; As a result of CE analysis, the purity was 97.1%, as shown in FIG. 8.

Example 5. Target Binding Activity of Anti-PD-L1/Anti-CD47 Heterodimeric Antibody Molecule The binding ability of the anti-PD-L1/anti-CD47 heterodimeric antibody to a single antigen was determined by enzyme-linked immunosorbent assay (ELISA).

Detailed procedure of the ELISA was as follows: Recombinant human PD-L1 (Sino Biological Inc., Cat. No. 10377-H08H) or human CD47 (Beijing ACROBiosystems, Cat. No. CD7-H5227) was coated on a 96-well high adsorption ELISA plate (Costar, Cat. No. 42592) using a carbonate buffer solution (0.05M) of pH 9.6 at a coating concentration of 1 μg/mL and a coating amount of 100 μL per well. The coating was performed at 4° C. overnight. The plate was washed with PBST five times. The plate was blocked with 300 μL/well of PBST containing 1% BSA and incubated for 1 hour at 25° C., and washed with PBST five times. A heterodimeric antibody sample and a control each serially diluted with PBST containing 1% BSA were added in an amount of 100 μL per well, and incubated at 25° C. for 1 hour. The plate was washed with PBST five times. Then, a horseradish peroxidase-labeled anti-human IgG antibody (Chemicon, Cat. No. AP309P) diluted 1:10000 with PBST containing 1% BSA was added in an amount of 100 μL per well, and incubated at 25° C. for 1 hour. The plate was washed with PBST five times. A colorimetric substrate TMB was added in an amount of 100 μL/well and developed for 10 minutes at room temperature. Color development was terminated by adding 100 μL/well of 1 M $H_2SO_4$. The absorbance at 450 nm was read on a microplate reader.

Figure 9:
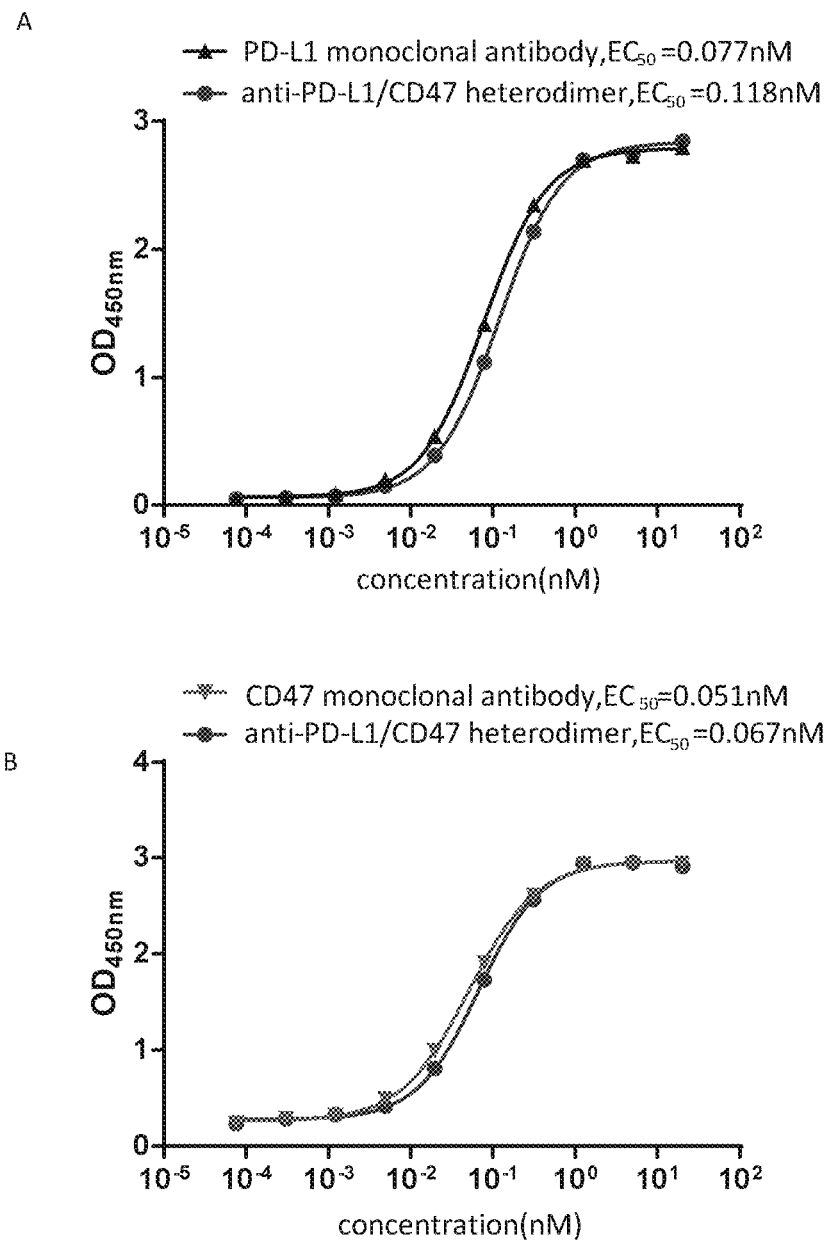
FIG. 9 Panel A shows the affinity of an anti-PD-L1/anti-CD47 heterodimeric antibody to PD-L1. Panel B shows the affinity of an anti-PD-L1/anti-CD47 heterodimeric antibody to CD47.

As a result, as shown in FIG. 9, Panel A, the anti-PD-L1/anti-CD47 heterodimeric antibody has high affinity for PD-L1, which is comparable to the antigen-binding activity of PD-L1 bivalent monoclonal antibody; as shown in FIG. 9, panel B, the anti-PD-L1/anti-CD47 heterodimeric antibody has high affinity for CD47, which is comparable to the antigen-binding activity of the CD47 bivalent monoclonal antibody.

Example 6. Simultaneous Binding Activity of Anti-PD-L1/Anti-CD47 Heterodimeric Antibody to Dual Targets Simultaneous binding ability of the anti-PD-L1/anti-CD47 heterodimeric antibody to two different antigens was determined by enzyme-linked immunosorbent assay (ELISA).

Detailed procedure of the ELISA was as follows: Recombinant human CD47 (Beijing ACROBiosystems, Cat. No. CD7-H5227) was coated on a 96-well high adsorption ELISA plate using a carbonate buffer solution of pH 9.6 at a coating concentration of 1 μg/mL and a coating amount of 100 μL per well. The coating was performed at 4° C. overnight. The plate was washed with PBST five times. The plate was blocked with 300 μL/well of PBST containing 1% BSA and incubated for 1 hour at 25° C., and washed with PBST five times. A heterodimeric antibody sample and a control each serially diluted with PBST containing 1% BSA were added in an amount of 100 μL per well, and incubated at 25° C. for 1 hour. The plate was washed with PBST five times. A botin-labeled PD-L1-Fc (Beijing Hanmi pharmaceutical) at 0.5 μg/mL, diluted with PBST containing 1% BSA, was added in an amount of 100 μL per well, and incubated at 25° C. for 1 hour. A streptavidin-horseradish peroxidase conjugate (BD Pharmingen, Cat. No. 554066) diluted 1:1000 with PBST containing 1% BSA was added in an amount of 100 μL per well, and incubated at 25° C. for 1 hour. The plate was washed with PBST five times. A colorimetric substrate TMB was added in an amount of 100 μL/well and developed for 10 minutes at room temperature. Color development was terminated by adding 100 μL/well of 1 M $H_2SO_4$. The absorbance at 450 nm was read on a microplate reader.

Figure 10:
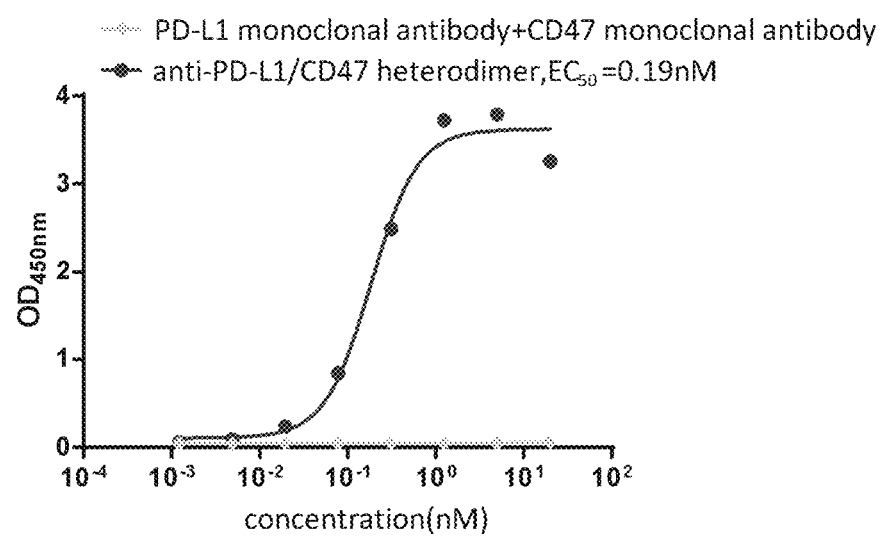
FIG. 10 shows that the combination of a PD-L1 monoclonal antibody and CD47 cannot simultaneously bind to PD-L1 and CD47, and only an anti-PD-L1/anti-CD47 heterodimeric antibody has the activity of binding to two antigens simultaneously.

As a result, as shown in FIG. 10, the combination of PD-L1 monoclonal antibody and CD47 cannot simultaneously bind to PD-L1 and CD47, and only the anti-PD-L1/anti-CD47 heterodimeric antibody has the activity of simultaneously binding to the two antigens.

Example 7. Binding of Anti-PD-L1/Anti-CD47 Heterodimeric Antibody to Tumor Cells/Red Blood Cells HCC827 tumor cells express PD-L1 and CD47, and red blood cells (RBCs) express only CD47. HCC827s and RBCs were mixed, and flow cytometry (FCM) was used to detect whether the heterodimer was selective for the binding of the two cells in the mixed cells.

The specific procedure of this method was as follows: HCC827 cells (purchased from ATCC® (American Type Culture Collection)) and RBC cells (collected from healthy people) were collected, and were washed once with cold DPBS (GIBCO, Cat. No. 14190-235) containing 2% FBS (Hyclone, Cat. No. SH30084.03). HCC827s were mixed at $1\times10^6$ cells/tube, and RBCs were mixed at $10\times10^6$ cells/tube, and were resuspended in 200 cold DPBS containing 2% FBS. A heterodimeric antibody sample and a control each serially diluted were added. The flow cytometry tube was incubated on ice for 30 minutes and was washed twice with DPBS containing 2% FBS. The cells were resuspended again in 200 μL of cold DPBS containing 2% FBS and 1:1000 diluted FITC-labeled anti-human IgG antibody (Beijing Zhongshan Goldenbridge, Cat. No. ZF0306), and was incubated on ice for 30 minutes in the dark. The cells were washed with DPBS containing 2% FBS, and then was resuspended in 500 μL cold DPBS. The cell suspension was analyzed on a flow cytometer (BD, FACS, Calibur), and the fluorescence intensity of each of the two cells in the mixed cells was read.

Figure 11:
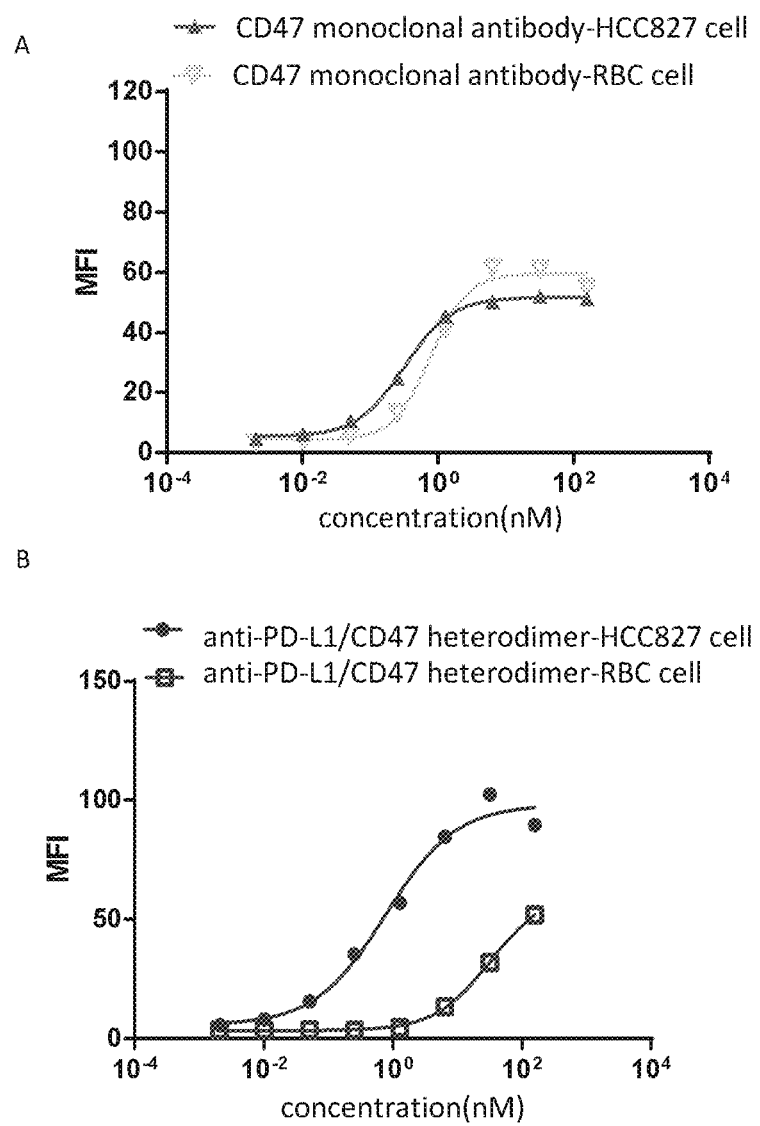
FIG. 11 Panels A and B show the binding activity of a CD47 monoclonal antibody and that of an anti-PD-L1/anti-CD47 heterodimer to HCC827 and RBC, respectively.

As a result, as shown in FIG. 11, the binding of CD47 monoclonal antibody to mixed HCC827s and RBCs is basically the same (Panel A); while the anti-PD-L1/anti-CD47 heterodimer has the tendency of binding to HCC827 cells expressing PD-L1 and CD47 while binds to RBC expressing only CD47 weakly, showing the selectivity of binding (Panel B).

Example 8. T Cell Regulatory Activity of Anti-PD-L1/Anti-CD47 Heterodimeric Antibody A mixed lymphocyte reaction (MLR) was used to determine the regulatory activity of anti-PD-L1/anti-CD47 heterodimeric antibody on T cell immune response.

Acquisition of human dendritic cells (DC): Human PBMC cells (Lonza, Cat. No. CC-2702) were collected by thawing. Human PBMC cells were resuspended in serum-free RPMI 1640 medium (GIBCO, Cat. No. 22400-089) at a cell density of $5\times10^6$/mL and were seeded in a cell culture flask, and were incubated in a $CO_2$ incubator at 37° C. for 90 minutes. The culture supernatant and suspended cells were discarded. The adherent cells were cultured in a complete medium (RPMI 1640 with 10% FBS), and 100 ng/mL GM-CSF (Sino Biological Inc., Cat. No. 10015-HNAH) and 100 ng/mL IL-4 (Sino Biological Inc., Cat. No. 11846-HNAE) were added. The cells were incubated for 3 days. After the medium was changed to fresh one, the cells were incubated for another 3 days. Then the medium was changed to a complete medium (RPMI 1640 with 10% FBS) containing 100 ng/mL GM-CSF, 100 ng/mL IL-4 and 20 ng/mL TNF-α, and the cells were incubated for 1 day to obtain DC cells.

Acquisition of human T cells: Human PBMC cells were collected by thawing. Such PBMCs and the PBMCs for inducing DC cells were from different individuals. T cells were isolated according the instruction manual of Pan T Cell Isolation Kit (Miltenyi Biotech, Cat. No. 5150414820). Briefly, PBMCs were washed once with DPBS, then resuspended at $10^7$ cells per 40 μL of separation buffer (DPBS containing 2 mM EDTA, 0.5% BSA, pH=7.2) (the following amounts are all based on $10^7$ cells), added with 10 μL Pan T cell Biotin Antibody Cocktail, and incubated at 4° C. for 5 minutes. After added with 30 μL of separation buffer and 20 μL of Pan Cell MicroBead Cocktail, the cells were incubated at 4° C. for 10 minutes. After passing through a MACS separation column, T cells were obtained.

The collected human DC cells and human T cells were resuspended in a complete medium (RPMI 1640 with 10% FBS) and seeded in a 96-well plate. The DC cells and T cells were seeded at $1\times10^4$/well and $1\times10^5$/well respectively, and were cultured in mixture. A heterodimeric antibody sample and a control each serially diluted with the complete medium were added. The plate was incubated in a $CO_2$ incubator at 37° C. for 5 days. After the incubation, the supernatant in the well was removed, and cytokine IFN-γ was detected according to the instruction manual of the kit (RayBiotech, Cat. No. ELH-IFNg).

Figure 12:
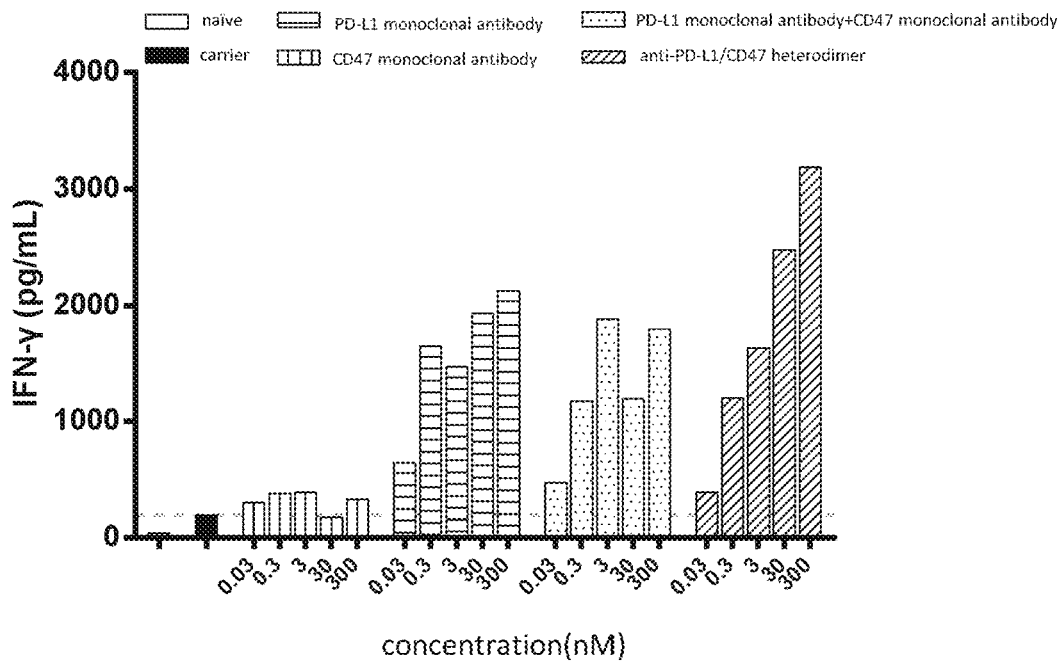
FIG. 12 shows the T cell regulatory activity of an anti-PD-L1/anti-CD47 heterodimeric antibody.

As shown in FIG. 12, human T cells are activated to secrete IFN-γ after stimulated by allogeneic DC cells. Adding PD-L1 antibody will enhance the activation of T cells and promote the secretion of cytokines. Anti-PD-L1/anti- CD47 heterodimeric antibody also shows strong T cell regulatory activity, significantly promoting the secretion of cytokine IFN-γ.

Example 9. Anti-PD-L1/Anti-CD47 Heterodimeric Antibody-Mediated Phagocytic Activity of Macrophages Against Tumor Cells Preparation of mature human macrophages: Human PBMC cells (Lonza, Cat. No. CC-2702) were collected by thawing. Human PBMC cells were resuspended in serum-free RPMI 1640 medium at a cell density of 5×10$^6$/mL and were seeded in a cell culture flask, and were incubated in a CO$_2$ incubator at 37° C. for 90 minutes. The culture supernatant and suspended cells were discarded. The adherent cells were cultured in a complete medium (RPMI 1640 with 10% FBS), and 25 ng/mL M-CSF (Sino Biological Inc., Cat. No. 10015-HNAH) were added. The cells were incubated for 7 days. Then the macrophages were collected and resuspended in a complete medium (RPMI 1640 with 10% FBS) containing 25 ng/mL M-CSF and 50 ng/mL IFN-γ (Sino Biological Inc., Cat. No. 11725-HNAS). The cell suspension was seeded in a 48-well cell culture plate at 50000 cells per well, and was incubated for 1 day to make the macrophage mature and ready for use.

Raji tumor cells were stained according to the instruction manual of CFSE kit (Life Technology, Cat. No. C34554). Briefly, CFSE was diluted with DPBS to a working concentration of 5 μM. After preheated at 37° C., Raji cells were collected by centrifuging at 1000 rpm for 5 minutes. After resuspended with preheated CFSE working solution, Raji cells were incubated at 37° C. for 15 minutes. The cells were washed once with the complete medium, resuspended in the complete medium, incubated for 30 minutes, washed twice with the complete medium, and then resuspended in the complete medium for use.

The 48-well plate was washed 3 times with the complete medium. The CFSE-stained Raji cells were pre-incubated with the heterodimer sample to be tested and the control for 15 minutes, then added to a 48-well culture plate, and incubated in a CO$_2$ incubator at 37° C. for 2 hours. After the incubation, the 48-well plate was washed three times with the complete medium, added with 10 μg/mL of wheat germ agglutinin, Alexa Fluor® 555 (fluorescent dye, Life technologies, No. W32464) diluted in the complete medium, and incubated for 15 minutes in the dark. The 48-well plate was washed three more times with the complete medium and fixed with 4% paraformaldehyde for 15 minutes. The 48-well plate was washed three more times with the complete medium, and added with the complete medium. The cells were counted by photographing with a fluorescence microscope. The calculation method of the phagocytic index (%) was: the number of phagocytosed green-labeled Raji cells/the number of the existent red-labeled macrophages× 100.

Figure 13:
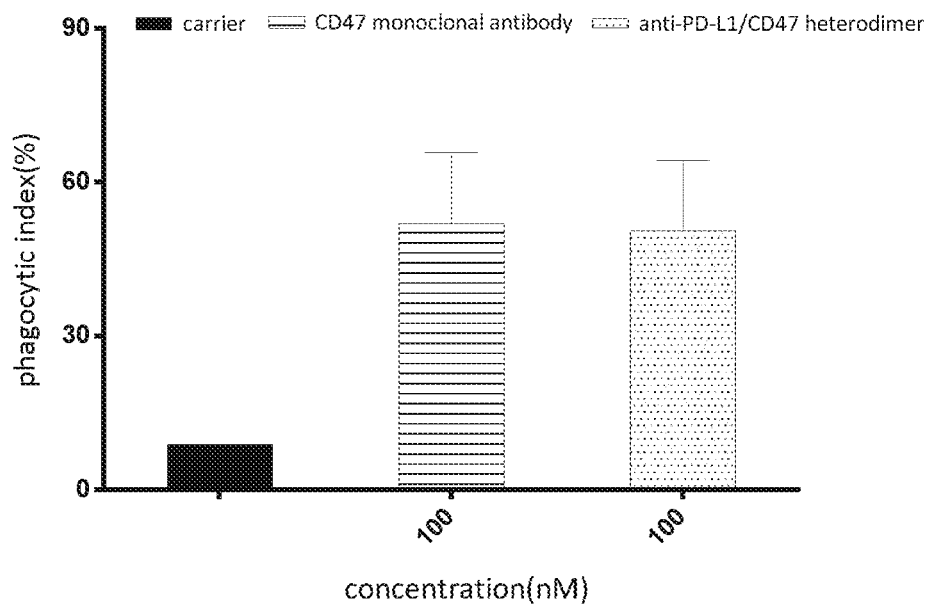
FIG. 13 shows the phagocytic activity of macrophages on tumor cells mediated by an anti-PD-L1/anti-CD47 heterodimeric antibody.

As shown in FIG. 13, anti-PD-L1/anti-CD47 heterodimeric antibody can mediate macrophages to phagocytose Raji tumor cells, which is comparable to the activity of CD47 monoclonal antibody.

The invention claimed is:

1. A bispecific antibody in the form of a heterodimer consisting of a first antibody, which comprises a first Fc chain and a first antigen-binding functional region that can specifically bind to human PD-L1; and a second antibody which comprises a second Fc chain and a second antigen-binding functional region that can specifically bind to human CD47;
   wherein the first antibody comprises a light chain variable region comprising the amino acid sequence of SEQ ID NO.: 2, a light chain constant region comprising the amino acid sequence of SEQ ID NO.: 4, a heavy chain variable region comprising the amino acid sequence of SEQ ID NO.: 6 and a heavy chain constant region comprising the amino acid sequence of SEQ ID NO.: 8; and
   wherein the second antibody comprises a light chain variable region comprising the amino acid sequence of SEQ ID NO.: 10, a light chain constant region comprising the amino acid sequence of SEQ ID NO.: 4, a heavy chain variable region comprising the amino acid sequence of SEQ ID NO.: 12 and a heavy chain constant region comprising the amino acid sequence of SEQ ID NO.: 14.

2. The bispecific antibody in the form of a heterodimer according to claim 1, wherein the first antigen-binding functional region and the second antigen-binding functional region are selected from a Fab fragment, a scFv fragment, and a variable domain fragment Fv.

3. The bispecific antibody in the form of a heterodimer according to claim 1, wherein the first antigen-binding functional region and the second antigen-binding functional region are both Fab fragments, or one of the first antigen-binding functional region and the second antigen-binding functional region is a Fab fragment, and the other is a scFv.

4. The bispecific antibody in the form of a heterodimer according to claim 1, wherein the first Fc chain and the first antigen-binding functional region covalently linked thereto, and the second Fc chain and the second antigen-binding functional region covalently linked thereto, when in a solution in which a reducing agent is present and which comprises no other polypeptide in addition to the first Fc chain and the first antigen-binding functional region covalently linked thereto, and the second Fc chain and the second antigen-antigen binding functional region covalently linked thereto, form less than 50% of homodimers based on the weight of all polypeptide chains.

5. A composition comprising the bispecific antibody in the form of a heterodimer according to claim 1, and a pharmaceutically acceptable carrier.

6. An isolated polynucleotide encoding the bispecific antibody in the form of a heterodimer according to claim 1.

7. The isolated polynucleotide according to claim 6, wherein the nucleotide sequence encoding the light chain variable region of the first antibody comprises SEQ ID NO:1, the nucleotide sequence encoding the light chain constant region of the first antibody comprises SEQ ID NO:3, the nucleotide sequence encoding the heavy chain variable region of the first antibody comprises SEQ ID NO:5, the nucleotide sequence encoding the heavy chain constant region of the first antibody comprises SEQ ID NO:7, the nucleotide sequence encoding the light chain variable region of the second antibody comprises SEQ ID NO:9, the nucleotide sequence encoding the light chain constant region of the second antibody comprises SEQ ID NO:3, the nucleotide sequence encoding the heavy chain variable region of the second antibody comprises SEQ ID NO:11, and the nucleotide sequence encoding the heavy chain constant region of the second antibody comprises SEQ ID NO:13.

8. A recombinant expression vector comprising the isolated polynucleotide according to claim 6.

9. The recombinant expression vector according to claim 8, wherein the expression vector is a plasmid vector X0GC.

10. A host cell comprising the isolated polynucleotide according to claim 6.

11. The host cell according to claim 10, wherein the host cell is selected from HEK293T, HEK293F, HEK293E, CHO-S, CHO-dhfr⁻, CHO/DG44, ExpiCHO, *Escherichia coli* BL21, BL21(DE3), *Pichia, Saccharomyces cerevisiae, Kluyveromyces lactis*, and *Hansenula polymorpha*.

12. The host cell according to claim 10, wherein the host cell is selected from human embryonic kidney cell HEK293, hamster ovary cell CHO, *Escherichia coli*, an insect cell, a plant cell, and a mammalian breast cell.

13. A method for producing a bispecific antibody in the form of a heterodimer, which comprises the steps of:
   1) expressing the isolated polynucleotide according to claim 6 in a host cell;
   2) Reducing the proteins respectively expressed in the host cell; and
   3) mixing the reduced proteins and oxidizing the mixture, and optionally comprises the step of separation and purification.

14. The method according to claim 13, wherein the host cell is selected from human embryonic kidney cell HEK293, hamster ovary cell CHO, *Escherichia coli*, a yeast, an insect cell, a plant cell, and a mammalian breast cell.

15. The method according to claim 13, wherein the reduction step comprises 1) performing a reduction reaction in the presence of a reducing agent selected from the group consisting of 2-mercaptoethylamine, dithiothreitol, tris (2-carboxyethyl) phosphine, and other chemical derivatives; and 2) removing the reducing agent.

16. The method according to claim 13, wherein the oxidation step is oxidation in the air, and further comprises an oxidation reaction in the presence of an oxidizing agent selected from the group consisting of L-dehydroascorbic acid and the chemical derivatives thereof.

17. The method according to claim 13, wherein the host cell is selected from HEK293T, HEK293F, or HEK293E, CHO-S, CHO-dhfr⁻, CHO/DG44, ExpiCHO, *Escherichia coli* BL21, BL21(DE3), *Pichia, Saccharomyces cerevisiae, Kluyveromyces lactis*, and *Hansenula polymorpha*.

18. A method for treating CD47+ B-cell lymphoma, comprising administering the bispecific antibody in the form of a heterodimer according to claim 1, to a subject in need thereof, wherein the subject is a mammalian, or a human subject.

* * * * *

SEQUENCE LISTING

```
<160> NUMBER OF SEQ ID NOS: 15

<210> SEQ ID NO 1
<211> LENGTH: 321
<212> TYPE: DNA
<213> ORGANISM: Artificial Sequence
<220> FEATURE:
<223> OTHER INFORMATION: nucleotide sequence of light chain variable
      region of anti-human PD-L1 antibody

<400> SEQUENCE: 1
gacatccaga tgacccagag ccctagcagc ctgagcgcta gcgtgggcga cagggtgacc      60
atcacctgca gggccagcca ggatgtgagc accgctgtgg cctggtatca acagaagccc     120
ggcaaggccc ccaagctgct gatctacagc gccagcttcc tgtacagcgg cgtgcccagc     180
agatttagcg gcagcggcag cggcaccgat ttcaccctga ccatcagcag cctgcagccc     240
gaggacttcg ccacctacta ctgccagcag tacctgtacc atcccgccac cttcggccag     300
ggcaccaagg tggagatcaa g                                              321

<210> SEQ ID NO 2
<211> LENGTH: 107
<212> TYPE: PRT
<213> ORGANISM: Artificial Sequence
<220> FEATURE:
<223> OTHER INFORMATION: amino acid sequence of light chain variable
      region of anti-human PD-L1 antibody

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30
```

```
Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Tyr His Pro Ala
                 85                  90                  95

Thr Phe Gly Gln Gly Thr Lys Val Glu Ile Lys
                100                 105
```

<210> SEQ ID NO 3
<211> LENGTH: 321
<212> TYPE: DNA
<213> ORGANISM: Artificial Sequence
<220> FEATURE:
<223> OTHER INFORMATION: nucleotide sequence of light chain constant
      region of anti-human PD-L1 antibody

<400> SEQUENCE: 3

```
cgaactgtgg ccgctccaag cgtcttcatt tttccaccct ctgacgaaca gctgaagtca      60
gggacagctt ccgtggtctg tctgctgaac aatttttacc ccaggaggc caaagtgcag     120 tggaaggtcg ataacgctct gcagagcgga aattctcagg agagtgtgac agaacaggac     180
tcaaaagatt ccacttatag cctgtctagt accctgacac tgtccaaggc agactacgaa     240
aagcataaag tgtatgcctg tgaggtcaca catcagggtc tgtcaagccc cgtcactaag     300
tccttcaatc gtggcgaatg c                                               321
```

<210> SEQ ID NO 4
<211> LENGTH: 107
<212> TYPE: PRT
<213> ORGANISM: Artificial Sequence
<220> FEATURE:
<223> OTHER INFORMATION: amino acid sequence of light chain constant
      region of anti-human PD-L1 antibody

<400> SEQUENCE: 4

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105
```

<210> SEQ ID NO 5
<211> LENGTH: 354
<212> TYPE: DNA
<213> ORGANISM: Artificial Sequence
<220> FEATURE:
<223> OTHER INFORMATION: nucleotide sequence of heavy chain variable
      region of anti-human PD-L1 antibody

<400> SEQUENCE: 5

```
gaggtgcagc tggtggagag cggaggagga ctggtgcagc ctggaggatc cctgagactg    60
agctgcgccg ccagcggctt caccttcagc gacagctgga tccactgggt gagacaggcc   120
cctggcaagg gcctggaatg gtggcctgg atctcccctt acggcggcag cacctactac    180
gccgacagcg tgaagggcag gttcaccatc agcgccgaca ccagcaagaa caccgcctac   240
ctgcagatga acagcctgag ggccgaggac accgccgtgt actactgcgc cagaagacac   300
tggcccggcg gattcgacta ctggggacag ggcaccctgg tgaccgtgag cgcc         354
```

<210> SEQ ID NO 6
<211> LENGTH: 118
<212> TYPE: PRT
<213> ORGANISM: Artificial Sequence
<220> FEATURE:
<223> OTHER INFORMATION: amino acid sequence of heavy chain variable
      region of anti-human PD-L1 antibody

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115
```

<210> SEQ ID NO 7
<211> LENGTH: 990
<212> TYPE: DNA
<213> ORGANISM: Artificial Sequence
<220> FEATURE:
<223> OTHER INFORMATION: nucleotide sequence of heavy chain constant
      region of anti- PD-L1 antibody

<400> SEQUENCE: 7

```
gcttcaacaa aaggaccttc cgtgtttcca ctggcaccct ctagtaagag tacttcagga    60
ggaaccgcag cactgggatg tctggtgaag gactacttcc cagagcccgt caccgtgtct   120
tggaacagtg gagcactgac ctccggggtc catacatttc ctgccgtgct gcagtcatcc   180
ggtctgtata gcctgagctc tgtggtcaca gtcccaagtt catccctggg cacccagaca   240
tacatctgca acgtgaatca caaaccttcc aatactaagg tcgacaagaa agtggaaccc   300
aagtcctgcg ataagaccca cacatgccct cctgtcctg ctcccgaact gctgggagga    360
ccctccgtct tcctgttccc ccccaagccc aaagacacac tgatgatcag caggacccct   420
gaagtgacct gcgtggtcgt ggacgtgagc cacgaggacc ccgaggtcaa gtttaactgg   480
tacgtggacg gcgtggaggt ccacaacgcc aagaccaagc cagggagga gcagtacgcc    540 agcacctaca gggtcgtgtc cgtgctgacc gtgctccacc aagattggct caacggcaag   600
```

```
gagtataagt gcaaagtcag caacaaggcc ctccccgccc ccatcgagaa aaccatcagc    660
aaggccaagg ccaaccgcgg ggaacctcaa gtgtataccc tccctcccag ccgggatgag    720
ctgaccaaga accaagtctc cctcttgtgc ctggtcaagg gattctaccc ttccgacatt    780
gccgtcgaat gggagagcaa tggccagccc gagaacaact acaagacaac ccccccgtc     840 ctgcgcagcg acggatcctt cttcctgtac tccaagctca ccgtggacaa gagccggtgg    900
caacagggca acgtgttctc ctgtagcgtg atgcacgaag ccctccacaa ccactatacc    960
cagaagagcc tgagcctcag ccccggcaaa                                      990

<210> SEQ ID NO 8
<211> LENGTH: 330
<212> TYPE: PRT
<213> ORGANISM: Artificial Sequence
<220> FEATURE:
<223> OTHER INFORMATION: amino acid sequence of heavy chain constant
      region of anti- PD-L1 antibody

<400> SEQUENCE: 8
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Leu Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Arg Ser Asp Gly Ser Phe Phe
        275                 280                 285

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 321
<212> TYPE: DNA
<213> ORGANISM: Artificial Sequence
<220> FEATURE:
<223> OTHER INFORMATION: nucleotide sequence of light chain variable
      region of anti-human CD47 antibody

<400> SEQUENCE: 9
aacatccaga tgacccagtc cccttccgcc atgagcgctt ccgtgggcga cagggtgacc    60
atcacatgca aggcctccca ggacatccac cgttatttaa gctggtttca gcagaagccc   120
ggcaaggtgc ccaagcacct gatctacagg gctaacaggc tggtgtccgg cgtgccttcc   180
aggttttccg gcagcggttc tggcaccgag tttaccctga ccatctcctc cctgcagccc   240
gaggacttcg ccacctacta ctgcctgcag tacgacgagt tcccctacac cttcggcggc   300
ggcaccaagg tggagatcaa g                                             321

<210> SEQ ID NO 10
<211> LENGTH: 107
<212> TYPE: PRT
<213> ORGANISM: Artificial Sequence
<220> FEATURE:
<223> OTHER INFORMATION: amino acid sequence of light chain variable
      region of anti-human CD47 antibody

<400> SEQUENCE: 10

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 11
<211> LENGTH: 360
<212> TYPE: DNA
<213> ORGANISM: Artificial Sequence
<220> FEATURE:
<223> OTHER INFORMATION: nucleotide sequence of heavy chain variable
      region of anti-human CD47 antibody

<400> SEQUENCE: 11
cagatgcagc tggtgcagtc cggcgccgag gtgaaaaagc ccggctcctc cgtgaaggtg    60
tcctgcaagg ccagcggctt caacatcaag gactactacc tgcactgggt gaggcaggct   120
```

```
cccggacagg ctctggagtg gatgggctgg atcgaccccg accagggcga taccgagtac    180
gcccagaagt tccagggccg ggtgacaatc accagggaca ggagcacctc caccgcctac    240
atggagctga ggtccctgag gtccgaggac accgccgtgt actactgcaa cgccgcttac    300
ggcagcagct cctaccccat ggactactgg ggccagggca aaccgtgac cgtgagctcc     360
```

```
<210> SEQ ID NO 12
<211> LENGTH: 120
<212> TYPE: PRT
<213> ORGANISM: Artificial Sequence
<220> FEATURE:
<223> OTHER INFORMATION: amino acid sequence of heavy chain variable
      region of anti-human CD47 antibody

<400> SEQUENCE: 12
```

Gln Met Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Gln Gly Asp Thr Glu Tyr Ala Gln Lys Phe
    50                  55                  60

Gln Gly Arg Val Thr Ile Thr Arg Asp Arg Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val Ser Ser
        115                 120

```
<210> SEQ ID NO 13
<211> LENGTH: 990
<212> TYPE: DNA
<213> ORGANISM: Artificial Sequence
<220> FEATURE:
<223> OTHER INFORMATION: nucleotide sequence of heavy chain constant
      region of anti-human CD47 antibody

<400> SEQUENCE: 13
```

```
gctagcacaa aaggaccttc cgtgtttcca ctggcaccct ctagtaagag tacttcagga    60
ggaaccgcag cactgggatg tctggtgaag gactacttcc cagagcccgt caccgtgtct    120
tggaacagtg gagcactgac ctccggggtc catacatttc ctgccgtgct gcagtcatcc    180
ggtctgtata gcctgagctc tgtggtcaca gtcccaagtt catccctggg cacccagaca    240
tacatctgca acgtgaatca caaaccttcc aatactaagg tcgacaagaa agtggaaccc    300
aagtcctgcg ataagaccca cacatgccct cctgtcctg ctcccgaact gctgggagga    360
ccctccgtct tcctgttccc ccccaagccc aaagacacac tgatgatcag caggaccct    420 gaagtgacct gcgtggtcgt ggacgtgagc cacgaggacc ccgaggtcaa gtttaactgg    480
tacgtggacg gcgtggaggt ccacaacgcc aagaccaagc caggagga gcagtacgcc     540 agcacctaca gggtggtcag cgtgctgacc gtgctgcacc aggattggct caacggcaag    600
gagtacaagt gcaaagtctc caacaaggcc ctgcccgccc ccatcgagaa gaccatctcc    660
aaggctaagg gacagcccag ggagcccaa gtgtacaccg agcctccag ccgggatgag     720 ctgaccaaga accaagtctc cctcacctgc ctggtcaagg gattctaccc ttccgacatt    780
```

```
gccgtcgaat gggagagcaa tggccagccc gagaacaact acaagacaac ccccccgtc    840 ctggatagcg acggatcctt cttcctgctc tccgtgctca ccgtcgacaa gagcagatgg    900
cagcagggca acgtgttcag ctgtagcgtg atgcacgagg ccctgcacaa ccactacacc    960
cagaagagcc tgtccctcag ccccggcaag                                     990
```

<210> SEQ ID NO 14
<211> LENGTH: 330
<212> TYPE: PRT
<213> ORGANISM: Artificial Sequence
<220> FEATURE:
<223> OTHER INFORMATION: amino acid sequence of heavy chain constant
      region of anti-human CD47 antibody

<400> SEQUENCE: 14

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Glu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Leu Ser Val Leu Thr Val Asp Lys Ser Arg Trp Gln Gln Gly Asn
    290                 295                 300
```

-continued

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 15
<211> LENGTH: 15
<212> TYPE: PRT
<213> ORGANISM: Artificial Sequence
<220> FEATURE:
<223> OTHER INFORMATION: lnker

<400> SEQUENCE: 15

Gly Gly Gly Gly Ser Gly Gly Gly Gly Ser Gly Gly Gly Gly Ser
1               5                   10                  15
```